(12) United States Patent
O'Brien

(10) Patent No.: US 6,849,602 B1
(45) Date of Patent: Feb. 1, 2005

(54) COMPOSITIONS FOR ALLEVIATING NEUROPATHIC PAIN WITH PROSAPOSIN RECEPTOR AGONISTS

(75) Inventor: John S. O'Brien, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/928,074

(22) Filed: Sep. 11, 1997

Related U.S. Application Data

(63) Continuation-in-part of application No. 08/611,307, filed on Mar. 5, 1996, now Pat. No. 6,271,196, and a continuation-in-part of application No. PCT/US97/04143, filed on Mar. 5, 1997.

(51) Int. Cl.[7] ............................................. A61K 38/10
(52) U.S. Cl. ........................................... 514/14; 514/2
(58) Field of Search ............................... 530/300, 324, 530/326, 327, 350; 514/14, 2

(56) References Cited

U.S. PATENT DOCUMENTS

| | | | |
|---|---|---|---|
| 5,470,582 A | 11/1995 | Supersaxo et al. | 424/489 |
| 5,571,787 A | 11/1996 | O'Brien et al. | 514/12 |
| 5,696,080 A | * 12/1997 | O'Brien et al. | 514/2 |
| 6,268,347 B1 | * 7/2001 | O'Brien | 514/14 |
| 6,559,124 B1 | 5/2003 | O'Brien et al. | |
| 6,590,074 B1 | 7/2003 | O'Brien et al. | |

FOREIGN PATENT DOCUMENTS

| | | |
|---|---|---|
| EP | 0246753 A2 | 11/1987 |
| EP | 0288243 A2 | 10/1988 |
| EP | 0405467 A2 | 1/1991 |

OTHER PUBLICATIONS

Hong et al., *Intracellular Adhesion Molecule–1 Expression Induced by Interleukin(IL)–1B or IB Fragment is blocked by an IL–1 Receptor Antagonist and a Soluble IL–1 Receptor.* Journal of Neuroimmunology 44(2):163–170 (Jun. 1993).

Kotani et al., *Prosaposin Facilities Sciatic Nerve Regeneration In Vivo*, Journal of Neurochemistry 66(5):2019–2025 (May 1996).

Albright, "Intrathecal Baclofen in Cerebral Palsy Movement Disorders," *Journal of Child Neuropathy II(Suppl. I)* S29–S35 (1996).

Banks et al., "Permeability of the Blood–Brain Barrier to Peptides: An Approach to the Development of Therapeutically Useful Analogs," *Peptides 13:* 1289–1294 (1992).

Bennett et al., "A peripheral mononeuropathy in rat that produces disorders of pain sensation like those seen in man," *Pain 33:* 87–107 (1988).

Bennett, "An Animal Model of Neuropathic Pain: A Review," *Muscle& Nerve 16:* 1040–1048 (1993).

Calcutt et al., "Tactile allodynia and formalin hyperalgesia in streptozoticin–diabetic rats: effects of insulin, aldose reductase inhibition and lidocaine" *Pain* 68:293–299 (1996).

Campana et al., "Prosaptide, a Peptide derived from Prosaposin, Includes Motor Endplate Sprouting and Prevents Taxol Neuropathy," *Society for Neurosciences, 21:554* (1995).

Hefti et al., "Chronic Administration Of Nerve Growth Factor and Other Neurotrophic Factors in the Brain," *Neurobiology of Aging 9:* 689–690 (1988).

Jackowski, "Neural Injury Repair: Hope for the Future as Barriers to Effective CNS Regeneration Become Clearer," *British Journal of Neurosurgery 9:* 303–317 (1995).

Kim et al., "An Experimental Model for Peripheral Neuropathy Produced by Segmental Spinal Nerve Ligation in the Rat," *Pain,* 50:355–363 (1992).

Kotani et al., "A Hydrophilic Peptide Comprising 18 Amino Acid Residues of the Prosaposin Sequence Has Neurotrophic Activity In Vitro and In Vivo," *J. Neurochem 66:* 2197–2220 (1996).

Lekan et al., "Behavioral reponses following an experimental neuropathy in primates," *Soc. Neurosci. Abst.* 18:287 (1992).

McMahon et al., "Peripheral neuropathies and neurotrophic factors: animal models and clinical perspectives," *Curr. Opinion in Neurobiology 5 :* 616–624 (1995).

Merck Manual, Sixteenth Edition (1992) Berkow, ed., Merck Research Laboratories, Rathway, NJ, pp. 1416–1419.

Myers, "The Pathogenesis of Neuropathic Pain," *Regional Anesthesia 20(3):* 173–184 (1995).

O'Brien et al., "Identification of the Neurotrophic Factor Sequence of Prosaposin," *FASEB J. 9:* 681–685 (1995).

Onoprienko et al., "Synthesis and Immunogenic properties of Peptides Corresponding to 59–72 and 25–36 sequences of Human IL–2," *Bioorg. Khim. 15(7):* 908–921 (1989) (English language abstract).

Pachner et al., "An Immunodominant Site of Acetylcholine Receptor," *Immunology Letters 20:* 199–204 (1989).

(List continued on next page.)

*Primary Examiner*—Brenda Brumback
*Assistant Examiner*—Robert C. Hayes
(74) *Attorney, Agent, or Firm*—Fish & Richardson P.C.

(57) ABSTRACT

The invention provides a method of alleviating neuropathic pain in a subject by administering a neuropathic pain alleviating amount of prosaposin receptor agonist to the subject. The invention also provides a method of inhibiting the onset of neuropathic pain in a subject by administering neuropathic pain alleviating amount of prosaposin receptor agonist to the subject. The present invention also provides prosaposin receptor agonists and the use of these agonists for stimulating neurite outgrowth, inhibiting neural cell death, promoting myelination and inhibiting neural demyelination. In addition, there is provided a method of inhibiting sensory or motor neuropathy by contacting neuronal cells with a composition comprising an effective inhibiting amount of prosaposin receptor agonist.

5 Claims, 10 Drawing Sheets

OTHER PUBLICATIONS

Palacek et al., "Responses of spinothalmic tract neurons to mechanical and thermal stimuli are increased in an experimental model of peripheral neuropathy in primates," *Soc. Neurosci. Abst.* 18:287 (1992).

Rudinger et al., "Characteristics of the Amino Acids as Components of a Peptide Hormone Sequence" in *Peptide Hormones, University Park Press*, (*1976*) pages 1–7.

Sano et al., "Protection by Prosaposin Against Ischemia–Induced Learning Disability and Neuronal Loss," *Biochem. Biophys. Res. Commun. 204* (2): 994–1000 (1994).

Schubert et al., "Multiple Influences of a Heparin–Binding Growth Factor on Neuronal Development" *The Journal of Cell Biology 104*: 635–643 (1987).

Seltzer et al. "A Novel Behavioral Model of Neuropathic Pain Disorders Produced in Rats by Partial Sciatic Nerve Injury," *Pain 43(2)*: 205–218 (1990).

Sprang et al., "Cytokine Structural Taxonomy and Mechanisms of Receptor Engagement," *Curr. Opinion, Struct. Biol. 3*: 816 (1993).

Triguero et al., "Capillary Depletion Method for Quantitation of Blood Brain Barrier Transport of Circulating Peptides and Plasma Proteins," *J. Neurochem. 54*: 1882–188 (1990).

Tsarbopoulos et al., "Peptide and Protein Mapping by $^{252}$Cf–Plasma Desorption Mass Spectrometry" *Anal. Biochem.*, V. 171 pages 113–123 (1988).

Wall et al., "Autonomy Following Peripheral Nerve Lesions: Experimental Anaethesia Dolorosa" *Pain 7*: 103–113 (1979).

Weiler et al., "Synthesis and Charachterization of a Bioactive 82–Residue Sphingolipid Activator Protein, Saposin C," *Journal of Molecular Neuroscience*, 4(3): 161–172 (1993).

* cited by examiner

COMPOSITIONS FOR ALLEVIATING NEUROPATHIC PAIN WITH PROSAPOSIN RECEPTOR AGONISTS

CLAIM OF PRIORITY

This application is a continuation-in-part of U.S. Ser. No. 08/611,307, filed on Mar. 5, 1996 now U.S. Pat. No. 6,271,196 and International application PCT/US97/04143, filed Mar. 5, 1997.

FIELD OF THE INVENTION

This invention relates generally to the field of pain therapy and more specifically to the use of prosaposin receptor agonist for the treatment of neuropathic pain.

BACKGROUND OF THE INVENTION

Neuropathic pain results from injury to a nerve. In contrast to the immediate pain (nociceptive pain) caused by tissue injury, neuropathic pain can develop days or months after a traumatic injury. Furthermore, while pain caused by tissue injury is usually limited in duration to the period of tissue repair, neuropathic pain frequently is long-lasting or chronic. Moreover, neuropathic pain can occur spontaneously or as a result of stimulation that normally is not painful.

The clinical causes of neuropathic pain are widespread and include both trauma and disease. For example, traumatic nerve compression or crush and traumatic injury to the brain or spinal cord are common causes of neuropathic pain. Furthermore, most traumatic nerve injuries also cause the formation of neuromas, in which pain occurs as a result of aberrant nerve regeneration. In addition, cancer-related neuropathic pain is caused when tumor growth painfully compresses adjacent nerves, brain or spinal cord. Neuropathic pain also is associated with diseases such as diabetes or alcoholism.

Unfortunately, neuropathic pain frequently is resistant to available drug therapies. In addition, current therapies have serious side-effects including, for example, cognitive changes, sedation, nausea and, in the case of narcotic drugs, addiction. Many patients suffering from neuropathic pain are elderly or have other medical conditions that particularly limit their tolerance of the side-effects associated with available drug therapy. The inadequacy of current therapy in relieving neuropathic pain without producing intolerable side-effects frequently is manifest in the depression and suicidal tendency of chronic pain sufferers.

Methods of alleviating neuropathic pain would improve the quality of life for many people suffering from pain due to trauma or disease. However, there currently are no effective drugs that relieve neuropathic pain without undesirable side-effects such as sedation and addiction. Thus, there is a need for methods of alleviating neuropathic pain without producing undesirable side-effects. The present invention satisfies this need and provides related advantages as well.

SUMMARY OF THE INVENTION

The present invention provides a method of alleviating neuropathic pain in a subject by administering a neuropathic pain alleviating amount of a prosaposin receptor agonist to the subject. For example, the invention provides a method of alleviating neuropathic pain resulting from a disorder of peripheral nerve, dorsal root ganglia, spinal cord, brainstem, thalamus or cortex in a subject by administering a neuropathic pain alleviating amount of a prosaposin receptor agonist having the amino acid sequence Cys-Glu-Phe-Leu-Val-Lys-Glu-Val-Thr-Lys-Leu-Ile-Asp-Asn-Asn-Lys-Thr-Glu-Lys-Glu-Ile-Leu (SEQ ID NO:1) or Thr-D-Ala-Leu-Ile-Asp-Asn-Asn-Ala-Thr-Glu-Glu-Ile-Leu-Tyr (SEQ ID NO:2). In addition, the invention provides a method of inhibiting the onset of neuropathic pain in a subject by administering a neuropathic pain alleviating amount of a prosaposin receptor agonist to the subject. The present invention also provides prosaposin receptor agonists, prosaposin-derived peptides and the use of these peptides for stimulating neurite outgrowth, inhibiting neural cell death, promoting myelination and inhibiting neural demyelination. In addition, there is provided a method of inhibiting sensory or motor neuropathy by contacting neuronal cells with a composition comprising a neuropathic pain alleviating amount of a prosaposin receptor agonist.

DETAILED DESCRIPTION OF THE INVENTION

Figure 1:
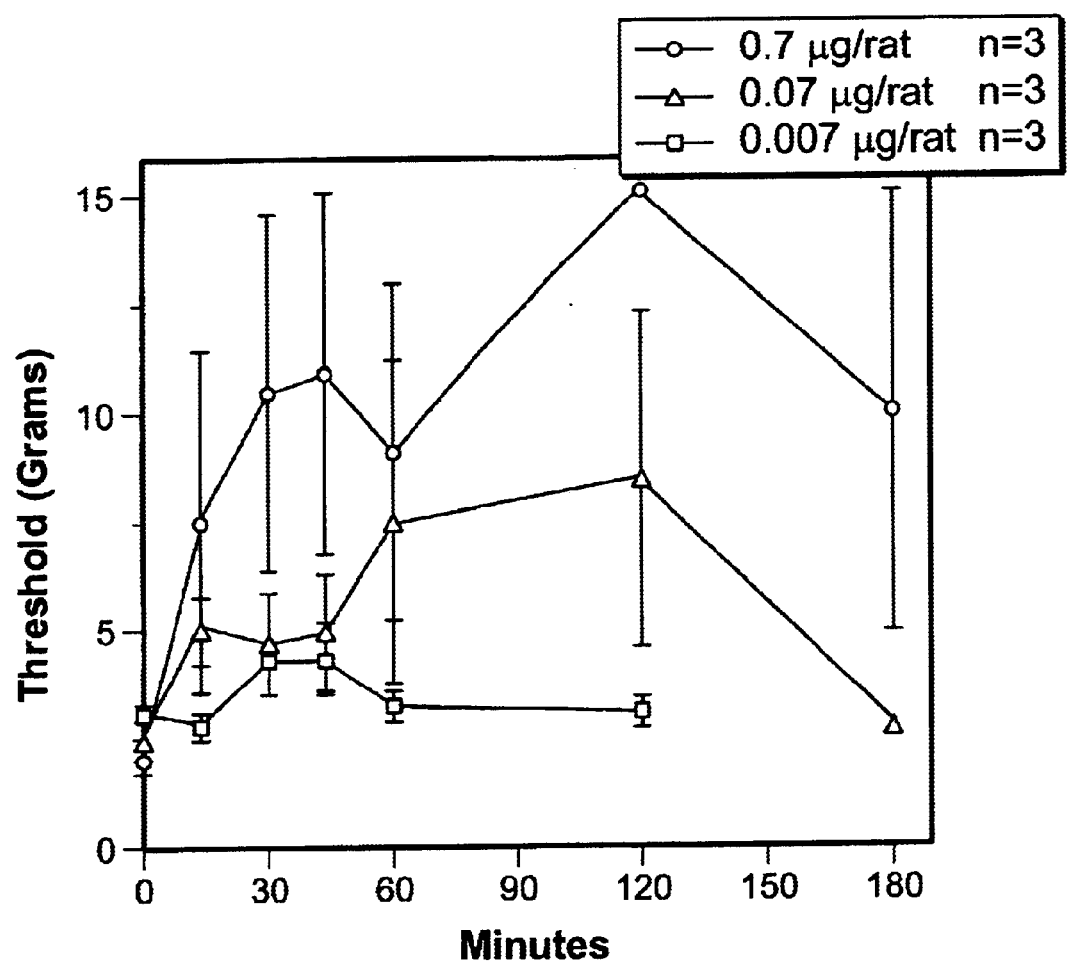
FIG. 1 shows the threshold of tactile allodynia before (time 0) and at various times after bolus injection of prosaposin-derived 22-mer peptide (SEQ ID NO:1) in Chung model rats.

The present invention provides a method of alleviating neuropathic pain in a subject by administering a neuropathic pain alleviating amount of a prosaposin receptor agonist to the subject. As disclosed herein, the method of the invention can alleviate neuropathic pain in a subject within 30 minutes of administration. Such a method is useful for alleviating neuropathic pain resulting from a disorder of peripheral nerve, dorsal root ganglia, spinal cord, brainstem, thaladus or cortex.

As used herein, the term "prosaposin receptor agonist" refers to a molecule which binds to any site on a cell to which prosaposin or a prosaposin-derived molecule can bind, and which thereby acts to alter the cell's function in the manner that prosaposin or a prosaposin-derived molecule acts. An agonist is any molecule that improves the activity of a different molecule; e.g., a hormone, which acts as an agonist when it binds to its receptor, thus triggering a biochemical response. A molecule that both binds to receptors and has an intrinsic effect is an agonist. A receptor agonist is a substance that mimics a specific hormone, is able to attach to that hormone's receptor, and thereby produces the same action that the hormone usually produces. Drugs are often designed as receptor agonists to treat diseases and disorders caused when the hormone is missing or depleted in a subject.

As used herein, the term "prosaposin receptor" refers to a site on a cell to which prosaposin or a prosaposin-derived molecule can bind, thereby acting to alter the cell's function. Prosaposin receptors may be cell surface proteins, other cell proteins, or glycosphingolipids. One putative prosaposin receptor protein is a 54–60 kilodalton (kDa) protein isolated from whole rat brain, rat cerebellum and mouse neuroblastoma cells using the plasma membrane P-100 fraction. The 54–60 kDa protein binds irreversibly to saposin C, a prosaposin derivative. The isolation of the putative prosaposin receptor is described in EXAMPLES XI and XII.

Prosaposin receptors may also be membrane lipids called glycosphingolipids. Glycosphingolipids are sphingolipids that have a carbohydrate head group and two hydrocarbon chains; one a fatty acid and the other a sphingosine derivative. Glycosphingolipids are important components of the myelin sheath, a structure which protects and insulates nerve fibers. Prosaposin binds glycosphingolipids such as gangliosides, cerebrosides and sulfatides with high affinity and facilitates their transfer from micelles to membranes (Sueda et al. *J. Biol. Chem.* (1993); Hiraiwa et al., *Proc. Natl. Acad. Sci. USA.*, 89: 11254–11258 (1992)). Gangliosides contain one or more sialic acid residues and are most abundant in the plasma membrane of neurons where they constitute approximately 6% of the total lipid mass. Although the function of gangliosides is largely unknown, they have been implicated in the stimulation of neuronal differentiation, neuritogenesis and nervous system repair.

In one embodiment, prosaposin receptor agonists may be prosaposin-derived peptides. As used herein, the term "active fragment of prosaposin" is synonymous with "prosaposin-derived peptide". A peptide useful in the invention is derived from prosaposin, which is a 517 amino acid protein originally identified as the precursor of four sphingolipid activator proteins (Kishimoto et al., *J. Lipid Res.*, 33:1255–1267 (1992)). Four adjacent tandem domains in prosaposin are proteolytically processed in lysosomes to generate saposins A, B, C, and D, which activate hydrolysis of glycosphingolipids by lysosomal hydrolases (O'Brien and Kishimoto, *FASEB J.*, 5:301–308 (1991)).

The unprocessed form of prosaposin is found in high concentrations in human and rat brain, where it is localized within neuronal surface membranes. During embryonic development, prosaposin mRNA is abundant in brain and dorsal root ganglia. Furthermore, prosaposin binds with high affinity to gangliosides, which stimulate neurite outgrowth, and promotes transfer of gangliosides from micelles to membranes.

The neurotrophic activity of prosaposin is consistent with its localization in neuronal cell populations (O'Brien et al., *Proc. Natl. Acad. Sci., USA* 91:9593–9596 (1994); Sano et al., *Biochem. Biophys. Res. Commun.,* 204:994–1000 (1994)). Prosaposin stimulates motor neurite outgrowth in vitro and in vivo and increases choline acetyltransferase activity, which is a marker of neuronal differentiation. In addition, prosaposin prevents cell death in neuroblastoma cells (O'Brien et al., supra, 1994; O'Brien et al., *FASEB J.* 9: 681–685 (1995)).

The neurotrophic activity of prosaposin is localized to saposin C, a domain of 80 amino acids. A 22-mer peptide corresponding to amino acids 8 to 29 of the saposin C domain (SEQ ID NO:1) stimulates neurite outgrowth and choline acetyltransferase activity and prevents cell death in neuroblastoma cells (O'Brien et al., supra, 1995).

Prosaposin or the prosaposin-derived 22-mer peptide (SEQ ID NO:1), for example, can modulate motor neuron function by promoting neurite outgrowth. Prior to the present invention, however, it was not known whether prosaposin or a peptide fragment of prosaposin could affect sensory neuron function. Moreover, the neurotrophic activity of prosaposin or a prosaposin-derived peptide in stimulating motor neurite outgrowth is evident only after a period of 24 to 48 hours (see, for example, O'Brien et al., supra (1994)). Neurotrophic activity of prosaposin or a prosaposin-derived peptide has not been demonstrated to occur in a shorter period of time.

In contrast, the present invention provides a method of alleviating neuropathic pain, which involves both sensory and motor neuron components. Furthermore, the method of the invention is effective in inhibiting or alleviating neuropathic pain in a matter of minutes rather than the hours or days previously demonstrated to be required for the neurotrophic activity of prosaposin or a prosaposin-derived peptide.

The effectiveness of the method of the invention in alleviating neuropathic pain was demonstrated using the well-recognized Chung rat model of peripheral neuropathy. In the Chung rat model, spinal nerve partial ligation of left spinal nerves L-5 and L-6 produces a long-lasting hypersensitivity to light pressure on the affected left foot. The hypersensitivity is similar to the pain experienced by humans with the neuropathic condition of causalgia as described in Kim and Chung, *Pain* 50:355–363 (1992).

Prior to administration of an active fragment of prosaposin, Chung model rats had a threshold of 3.0 to 4.0 g before the affected foot was withdrawn in response to pressure (Von Frey hairs) (see FIG. 1). After administration of an active fragment of prosaposin (prosaposin-derived 22-mer; SEQ ID NO:1), neuropathic pain was alleviated, as evidenced by a greater tolerance to pressure before the affected foot was withdrawn. The effect of the active fragment of prosaposin occurred within 15 minutes and was sustained for 3 hours following administration as shown in FIG. 1.

This rapid relief of neuropathic pain is in stark contrast to the delayed neurotrophic effects previously reported for prosaposin and peptides derived from prosaposin.

A prosaposin receptor agonist such as the prosaposin-derived peptide SEQ ID NO:2 also alleviated pain in a rat model of painful diabetic neuropathy. As described in EXAMPLE III, peptide SEQ ID NO:2 reduced allodynia in rats with short-term insulin-deficient diabetes induced by the selective β cell toxin, streptozotocin (STZ). Thus, a prosaposin receptor agonist of the invention can be used to alleviate a variety of types of neuropathic pain including mechanical pain, as exemplified by the Chung rat model, and metabolic pain, as exemplified by the use of these peptides in reducing pain in diabetic rats.

As used herein, the term "neuropathic pain" means pain resulting from injury to a nerve. Neuropathic pain is distinguished from nociceptive pain, which is the pain caused by acute tissue injury involving small cutaneous nerves or small nerves in muscle or connective tissue. Pain involving a nociceptive mechanism usually is limited in duration to the period of tissue repair and generally is alleviated by available analgesic agents or opioids as described in Myers, *Regional Anesthesia* 20:173–184 (1995).

Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Unlike nociceptive pain, neuropathic pain generally is resistant to opioid therapy (Myers, supra (1995)).

The method of the invention is useful in alleviating neuropathic pain resulting from a disorder of peripheral nerve, dorsal root ganglia, spinal cord, brainstem, thalamus or cortex. As used herein, the term "disorder" means any trauma, injury, disease or condition resulting in neuropathic pain.

The method of the invention is useful in alleviating neuropathic pain regardless of the etiology of the pain. For example, a method of the invention can be used to alleviate neuropathic pain resulting from a peripheral nerve disorder such as neuroma; nerve compression; nerve crush, nerve stretch or incomplete nerve transsection; mononeuropathy or polyneuropathy. A method of the invention also can be used to alleviate neuropathic pain resulting from a disorder such as dorsal root ganglion compression; inflammation of the spinal cord; contusion, tumor or hemisection of the spinal cord; tumors of the brainstem, thalamus or cortex; or trauma to the brainstem, thalamus or cortex (see, for example, TABLE 1).

The method of the invention can be useful, for example, to alleviate neuropathic pain resulting from a neuroma, which can develop readily after traumatic injury to nerve, especially when a whole nerve is severely crushed or transsected. In a neuroma, the neurite outgrowth that normally regenerates a peripheral nerve is aberrant or misguided due, for example, to a physical obstruction such as scar tissue. Thus, a regenerating nerve fiber is entangled in an environment in which mechanical and physical factors precipitate abnormal electrophysiologic activity and pain (Myers, supra (1995)). An amputation neuroma, for example, can cause phantom pain or can cause pain triggered by the use of a limb prosthesis. As disclosed herein, such neuropathic pain can be alleviated by administration of a prosaposin receptor agonist according to a method of the invention.

Nerve compression also results in neuropathic pain that can be treated using the method of the

TABLE 1

| Nerve |
| --- |
| Neuroma (amputation, nerve transsection) |
| Nerve compression (entrapment neuropathies, tumors) |
| Nerve crush, stretch or incomplete transsection (trauma) |
| Mononeuropathy |
| |
| Diabetes mellitus |
| Irradiation |
| Ischemia |
| Vasculitis |
| Polyneuropathy |
| |
| Post-polio syndrome |
| Diabetes mellitus |
| Alcohol |
| Amyloid |
| Toxic |
| HIV |
| Hypothyroidism |
| Uremia |
| Vitamin deficiencies |
| Chemotherapy (vincristine, cisplatinum, paclitaxel) |
| ddC (zalcitabine) |
| Fabry's disease |
| Dorsal root ganglion |
| |
| Compression (disk, tumor, scar tissue) |
| Root avulsion |
| Inflammation (postherpetic neuralgia) |
| Spinal cord |
| |
| Contusion |
| Tumor |
| Hemisection |
| Brainstem, thalamus, cortex |
| |
| Infarction, tumors, trauma | invention. Nerve compression can be abrupt, as in the case of traumatic nerve crush, or can be prolonged and moderate, secondary to tumor growth or scar formation in the proximity of a major nerve bundle. Compression neuropathy can occur as a result of changes in blood flow to a nerve, causing severe ischemia and consequent nerve injury (Myers, supra (1995)).

Administration of a prosaposin receptor agonist according to the method of the invention also can alleviate neuropathic pain resulting from a mononeuropathy or polyneuropathy. As used herein, a neuropathy is a functional disturbance or pathological change in the peripheral nervous system and is characterized clinically by sensory or motor neuron abnormalities. The term mononeuropathy indicates that a single peripheral nerve is affected, while the term polyneuropathy indicates that several peripheral nerves are affected.

The etiology of a neuropathy can be known or unknown (see, for example, Myers, supra (1995); Galer, *Neurology* 45(*suppl* 9):S17–S25 (1995); Stevens and Lowe, *Pathology*, Times Mirror International Publishers Limited, London (1995)). Known etiologies include complications of a disease or toxic state; for example, diabetes is the most common metabolic disorder causing neuropathy. The method of the invention alleviates the neuropathic pain of a mononeuropathy resulting, for example, from diabetes, irradiation, ischemia or vasculitis. The method of the invention also alleviates the neuropathic pain of a polyneuropathy resulting, for example, from post-polio syndrome, diabetes, alcohol, amyloid, toxins, HIV, hypothyroidism, uremia, vitamin deficiencies, chemotherapy, ddC or Fabry's disease (see TABLE 1). The method of the invention particularly is useful in alleviating post-polio myalgia. The method of the invention also can alleviate neuropathic pain of unknown etiology.

As disclosed herein, a prosaposin receptor agonist, for example, an active fragment of prosaposin, also can be useful in alleviating neuropathic pain or in stimulating neurite outgrowth, inhibiting neural cell death, promoting myelination or inhibiting demyelination or in inhibiting sensory neuropathy. The term "active fragment of prosaposin," as used herein, means a peptide that has an amino acid sequence corresponding to an amino acid sequence of prosaposin and that has activity in alleviating neuropathic pain or in stimulating neurite outgrowth, inhibiting neural cell death, promoting myelination or inhibiting demyelination or in inhibiting sensory or motor neuropathy.

As used herein, the term "inhibiting neuropathic pain" or "alleviating neuropathic pain" refers to any diminution in the severity of neuropathic pain. In a human subject, a prosaposin receptor agonist reduces the severity of neuropathic pain such that the subject's suffering is diminished and quality of life is improved. A prosaposin receptor agonist, for example, an active fragment of prosaposin, also can alleviate neuropathic pain in any one of a number of well-established animal models of neuropathic pain as described further below (also see Bennett, *Muscle & Nerve* 16:1040–1048 (1993)). As used herein, the term "active fragment of prosaposin" is synonymous with "prosaposin-derived peptide".

In one embodiment, the prosaposin receptor agonist in the invention is a prosaposin receptor agonist of 14 to 20 amino acids which has the amino acid sequence $LIRX_1NN\ X_2T\ X_3\ X_4\ X_3\ X_1\ X_1$, where $X_1$ is any amino acid; $X_2$ is any amino acid, but not L or R; $X_3$ is a charged amino acid; and $X_4$, when present, is a charged amino acid.

The prosaposin receptor agonist preferably contains the amino acid sequence Leu-Ile-Asp-Asn-Asn-Lys-Thr-Glu-Lys-Glu-Ile-Leu (SEQ ID NO:3), which corresponds to amino acids 18 to 29 of saposin C. More preferably, an active fragment of prosaposin has the amino acid sequence Cys-Glu-Phe-Leu-Val-Lys-Glu-Val-Thr-Lys-Leu-Ile-Asp-Asn-Asn-Lys-Thr-Glu-Lys-Glu-Ile-Leu (SEQ ID NO:1), which corresponds to amino acids 8 to 29 of saposin C, or the amino acid sequence Thr-D-Ala-Leu-Ile-Asp-Asn-Asn-Ala-Thr-Glu-Glu-Ile-Leu-Tyr (SEQ ID NO:2), which corresponds to amino acids 16 to 29 of saposin C but which has been modified by a D-alanine for lysine substitution at position 2; an alanine for lysine substitution at position 8; a deletion of lysine at position 11 and the addition of a C-terminal tyrosine residue (see TABLE 2). Such modifications can be useful for increasing peptide stability or uptake across the blood-brain barrier as described below. As used herein, D-alanine can be represented by D-Ala or X.

An active fragment of prosaposin can have about 12 amino acids to about 80 amino acids, which is the full-length of saposin C. Preferably, an active fragment of prosaposin has about 12 amino acids to about 40 amino acids and, more preferably, about 14 amino acids to about 22 amino acids.

TABLE 2

| PEPTIDE | SEQUENCE | SEQ ID NO: |
|---|---|---|
| Prosaposin-derived 22-mer | CEFLVKEVTKLIDNNKTEKEIL | 1 |
| Prosaposin-derived 14-mer | TXLIDNNATE-EILY | 2 |
| Prosaposin-derived 12-mer | LIDNNKTEKEIL | 3 | where X = D-alanine

For use in alleviating neuropathic pain in a human subject, an active fragment of human prosaposin, such as SEQ ID NO:1 or SEQ ID NO:2, is preferred. However, an active fragment derived from another mammalian prosaposin also is useful in alleviating neuropathic pain according to the method of the invention. Thus, for example, an active fragment of mouse prosaposin, rat prosaposin, guinea pig prosaposin or bovine prosaposin such as SEQ ID NOS: 4 through 7 also can be useful in alleviating neuropathic pain in a subject.

The amino acid sequence of an active fragment of human prosaposin (SEQ ID NO:1), which corresponds to amino acids 8 to 29 of saposin C, is well conserved among other species, as shown in TABLE 3. In particular, adjacent asparagine (N) residues are conserved among human, mouse, rat, guinea pig and bovine prosaposins. In addition, a leucine (L) residue is conserved 3 to 4 residues toward the N-terminus of the two asparagine residues and one or more charged residues (aspartic acid (D), lysine (K), glutamic acid (E) or arginine (R)) are conserved 2 to 8 residues toward the C-terminus of the two asparagine residues. Each of these well-conserved residues is underlined in TABLE 3.

TABLE 3

| SPECIES | SEQUENCE | SEQ ID NO. |
|---|---|---|
| Human | CEFLVKEVTKLIDNNKTEKEIL | 1 |
| Mouse | CQFVMNKFSELIVNNATE-ELLY | 4 |
| Rat | CQLVNRKLSELIINNATE-ELL | 5 |
| Guinea Pig | CEYVVKKVMLLIDNNRTEEKII | 6 |
| Bovine | CEFVVKEVAKLIDNNRTEEEIL | 7 |

The well-conserved adjacent asparagine residues, leucine residue and charged residues described above can be important for the activity of an active fragment of prosaposin in alleviating neuropathic pain or in stimulating neurite outgrowth, inhibiting neural cell death, promoting myelination or inhibiting demyelination or in inhibiting or motor neuropathy. For example, the prosaposin-derived 22-mer (SEQ ID NO:1) or the prosaposin-derived 14-mer (SEQ ID NO:2) is a prosaposin receptor agonist, an active fragment of prosaposin, which reduces the painful allodynia seen in the Chung rat model of peripheral neuropathy, as disclosed in EXAMPLE I (see FIGS. 1 and 2). In contrast, a mutant 22-mer (SEQ ID NO8), which differs from SEQ ID NO:1 in having an aspartic acid residue (D) in place of the first conserved asparagine (see TABLE 4), lacks activity in alleviating neuropathic pain as assayed using Chung rats (see EXAMPLE I).

TABLE 4

| PEPTIDE | SEQUENCE | SEQ ID NO: |
|---|---|---|
| Prosaposin-derived 22-mer | CEFLVKEVTKLIDNNKTEKEIL | 1 |
| Mutant 22-mer | CEFLVKEVTKLIDDNKTEKEIL | 8 |
| Prosaposin-derived 14-mer | TXLIDNNATE-EILY | 2 |
| Mutant 14-mer M-1 | TKLIDNDKTEKEIL | 9 |
| Mutant 14-mer M-2 | TKSIDNNKTEKEIL | 10 | where X = D-alanine

The activity of a peptide in alleviating neuropathic pain also can correlate with neurotrophic activity. For example, the prosaposin-derived 22-mer (SEQ ID NO:1) and the prosaposin-derived 14-mer (SEQ ID NO:2) alleviate neuropathic pain and have neurotrophic activity. In addition, the mutant 22-mer (SEQ ID NO:8) is inactive in alleviating neuropathic pain as described above and lacks neurotrophic activity, further indicating that activity in alleviating neuropathic pain can correlate with neurotrophic activity. The mutant 14mer peptide M-1 (SEQ ID NO:9), which has a substitution of the second conserved asparagine residue, lacks neurotrophic activity, indicating that peptide SEQ ID NO:9 also is inactive in alleviating neuropathic pain. The mutant 14-mer peptide M-2 (SEQ ID NO:10), which has a substitution of the conserved leucine residue, lacks neurotrophic activity, indicating that peptide SEQ ID NO:10 is inactive in alleviating neuropathic pain. In contrast, the prosaposin-derived 12-mer peptide (SEQ ID NO:3), which has the conserved adjacent asparagines, leucine and charged residues described above, is active as a neurotrophic factor. Thus, the prosaposin-derived 12-mer peptide (SEQ ID NO:3) also can alleviate neuropathic pain according to the method of the invention.

Prosaposin receptor agonists, including prosaposin-derived peptides and neurotrophic analogs thereof, possess significant therapeutic applications in promoting functional recovery after toxic, traumatic, ischemic, degenerative or inherited lesions to the peripheral or central nervous system. In addition, these peptides can promote myelination or inhibit demyelination, thereby counteracting the effects of demyelinating diseases. Furthermore, such peptides stimulate the outgrowth of neurons and inhibit programmed cell death in neuronal tissues. The active neurotrophic and myelinotrophic peptides of the invention have between about 12 or 14 and about 50 amino acids and preferably include the non-naturally occurring prosaposin sequence shown in SEQ ID NO:2. For example, the active neurotrophic and myelinotrophic peptides of the invention have between 14 and about 50 amino acids and include the non-naturally occurring prosaposin sequence shown in SEQ ID NO:2.

In another embodiment of the present invention, there is provided a method of stimulating neurite outgrowth, inhibiting neural cell death, promoting myelination or inhibiting demyelination in differentiated or undifferentiated neuronal cells by administering to the neuronal cells an effective amount of a neurite outgrowth or myelin-facilitating peptide having between about 12 and about 50 amino acids and preferably including the peptide shown in SEQ ID NO:2. In the methods of the invention for stimulating neurite outgrowth, inhibiting neural cell death, promoting myelination or inhibiting demyelination, an effective amount of a peptide having, for example, between 14 and about 50 amino acids and including the peptide shown in SEQ ID NO:2 can be used.

As used herein, the term "stimulating neurite outgrowth" refers to inducing or increasing the outgrowth of neural processes from neural cells. Neurite outgrowth may occur in differentiated or undifferentiated neural cells. For example, in differentiated cells, neurite outgrowth may be from from dorsal root ganglion explants, sympathetic ganglia explants, or nodose ganglion explants. Neurite outgrowth responses may also occur in neoroblastoma cells, such as NS20Y neuroblastoma cells or PC12 pheocromocytoma cells. As used herein, the term "inhibiting neural cell death" refers to the inhibition of the death of neural cells. Necrosis and apoptosis are two basic processes by which cells may die. In necrosis, cell death usually is a result of cell injury. The cells generally swell and lyse. The cell contents ultimately spill into the extracellular space. By contrast, apoptosis is a mode of cell death in which single cells are deleted in the midst of living tissues. Apoptosis accounts for most of the programmed cell death in tissue remodeling and for the cell loss that accompanies atrophy of adult tissues following withdrawal of endocrine and other growth stimuli. As used herein, the term "promoting myelination" refers to promoting the formation of a myelin sheath, a sheath of white, fatty protein (myelin) that covers and acts as an electrical insulator for nerve fibers. Oligodendrocytes form myelin in the central nervous system. Schwann cell form myelin in the peripheral nervous system. As used herein, the term "inhibiting demyelination" refers to the inhibition of the destruction of myelin sheaths that surrounds nerve fibers, which results in the loss of function of those nerves. In several diseases, the body attacks its own nervous system, destroying the myelin sheath that protects the nerve cells. This demyelination prevents the nerves from carrying signals properly, and afflicted persons can experience problems with muscular coordination, vision and other sensory problems, and paralysis. Several diseases that result in demyelination of nerve fibers include multiple sclerosis, acute disseminated leukoencephalitis, progressive multifocal leukoencephalitis, metachromatic leukodystrophy and adrenal leukodystrophy.

The ability of any such peptide to stimulate neurite outgrowth, inhibit neural cell death, promote myelination or inhibit demyelination readily can be determined by one skilled in the art using the procedures described in EXAMPLES IV to VII. Methods for assaying the abilities of these peptides to promote myelination and to inhibit demyelination are set forth in EXAMPLES VI and VII below.

The present invention also provides a method of inhibiting sensory neuropathy by contacting neuronal cells with a composition comprising an effective inhibiting amount of a prosaposin receptor agonist, for example, an active fragment of prosaposin. The invention provides, for example, a method of inhibiting sensory neuropathy by contacting neuronal cells with a composition comprising an effective inhibiting amount of a peptide having the sequence shown as SEQ ID NO:1 or SEQ ID NO:2.

As described herein in EXAMPLE X, a prosaposin-derived peptide can be useful in inhibiting sensory neuropathy. In a mouse model in which sensory neuropathy is induced by taxol administration, a loss of thermal sensation is normally seen. However, in taxol-treated mice given 100 $\mu$g/kg of peptide SEQ ID NO:1, the loss of thermal sensation was inhibited. These results indicate that prosaposin-derived peptides can be a neurotrophic factor for both sensory and motor neurons.

A peptide useful in the methods of the invention also can be, for example, SEQ ID NOS:11 through 19 (see TABLE 5). For example, sequence alignment of the prosaposin-derived 22-mer peptide SEQ ID NO:1 with cytokines and growth factors indicates sequence similarity to a number of human (h) cytokines including hCNTF, hIL-6, hIL-2, hIL-3, hIL1-$\gamma$, erythropoietin (hEPO), human leukocyte inhibitory factor (hLIF), the hIL-1 $\beta$ chain and oncostatin-M (hONC-M). SEQ ID NOS: 11 through 19, like the active fragment of prosaposin SEQ ID NO:1, contain two asparagine residues that are adjacent or separated by one amino acid. In addition, the cytokine-derived peptide sequences can contain a leucine (L) or isoleucine (I) residue three to four residues toward the N-terminus of the two asparagine residues and one or more charged residues (aspartic acid (D), lysine (K), glutamic acid (E), or arginine (R)) two to eight residues toward the C-terminus of the two asparagine residues, as is seen in the active fragment of prosaposin (22-mer; SEQ ID NO:1). Each of these residues is underlined in TABLE 5.

Models of cytokine-receptor binding (Sprang and Bazan, *Curr. Opin. Struct. Biol.*, 3:816 (1993)) have highlighted the evolutionary conservation of a four-helical bundle structure common to many cytokines. Each of the cytokine or growth-factor sequences related to the prosaposin-derived sequence SEQ ID NO:1 is located between helices A and B (AB loop) or within helix C of the cytokine.

TABLE 5

| CYTO-KINE | SEQUENCE | LOCATION | SEQ ID NO: |
|---|---|---|---|
| Prosaposin | CEFLVKEVTKLIDNNKTEKEIL | — | 1 |
| hCNTF | YVKHQGLNKNINLDSVDGVP | AB loop | 11 |
| hIL-6 | EALAENNLNLPKMAG | AB loop | 12 |
| hIL-2 | LQMILNGINNYKNPKLT | AB loop | 13 |
| hIL-3 | ILMENNLRRPNL | AB loop | 14 |
| hIL1-γ | FYLRNNQLVAGTL | AB loop | 15 |
| hEPO | AEHCSLNENITVPDTKV | AB loop | 16 |
| hLIF | YTAQGEPFPNNVEKLCAP | AB loop | 17 |
| hIL-1β | FNKIEINNKLEFESA | Helix C | 18 |
| hONC-M | RPNIGLRNNIYCMAQLL | Helix C | 19 |

The structurally related cytokine and growth factor-derived peptides SEQ ID NOS: 11 through 19 also can be useful in methods of alleviating neuropathic pain. Peptides SEQ ID NOS: 11 through 19 can be assayed for activity in alleviating neuropathic pain using, for example, the Chung rat model described in EXAMPLE I; a model of diabetic neuropathy as described in EXAMPLE III assays described by Wall et al., *Pain* 7:103–113 (1979); Bennett and Xie, *Pain* 33:87–107 (1988); Lekan et al., *Soc. Neurosci. Abstr.* 18:287 (1992) or Palacek et al., *Soc. Neurosci. Abstr.* 18:287 (1992); or other assays for neuropathic pain.

The cytokine and growth factor-derived peptides SEQ ID NOS: 11 through 19 also can be useful in methods of stimulating neurite outgrowth, inhibiting neural cell death, promoting myelination or inhibiting demyelination or in methods of inhibiting sensory or motor neuropathy. A peptide having between about 14 and about 50 amino acids and including the active neurotrophic region contained within one of sequences SEQ ID NOS: 11 through 19 can be assayed for the ability to stimulate neurite outgrowth as described in EXAMPLE IV; or assayed for the ability to inhibit neural cell death as described in EXAMPLE V; or for the ability to promote myelination as described in EXAMPLE VI; or for the ability to inhibit demyelination as described in EXAMPLE VII; or for the ability to inhibit sensory neuropathy as described in EXAMPLE X.

A prosaposin receptor agonist useful in alleviating neuropathic pain can be identified by screening a large collection, or library, of random peptides or peptides of interest using, for example, one of a number of animal models of neuropathic pain. Such prosaposin receptor agonists of interest can be, for example, the cytokine and growth factor-derived peptides SEQ ID NOS:11 through 19, which have amino acid sequences related to an active fragment of prosaposin (SEQ ID NO:1). Peptides of interest also can be, for example, a population of peptides related in amino acid sequence to SEQ ID NO:1 by having the conserved asparagine residues, leucine/isoleucine residue and one or more charged residues at the positions corresponding to the positions in which these residues are found in SEQ ID NO:1 but also having one or more amino acids that differ from the amino acids of SEQ ID NO:1.

Peptide libraries include, for example, tagged chemical libraries comprising peptides and peptidomimetic molecules. Peptide libraries also comprise those generated by phage display technology. Phage display technology includes the expression of peptide molecules on the surface of phage as well as other methodologies by which a protein ligand is or can be associated with the nucleic acid which encodes it. Methods for the production of phage display libraries, including vectors and methods of diversifying the population of peptides which are expressed, are well known in the art (see, for example, Smith and Scott, *Methods Enzymol.* 217:228–257 (1993); Scott and Smith, *Science* 249:386–390 (1990); and Huse, WO 91/07141 and WO 91/07149). These or other well known methods can be used to produce a phage display library, from which the displayed peptides can be cleaved and assayed for activity in alleviating neuropathic pain or other neurotrophic or myelinotrophic activity as described herein. If desired, a population of peptides can be assayed for activity, and an active population can be subdivided and the assay repeated in order to isolate an active peptide from the population. Other methods for producing peptides useful in the invention include, for example, rational design and mutagenesis based on the amino acid sequences of active fragments of prosaposin such as SEQ ID NO:1 and SEQ ID NO:2, for example.

As disclosed herein, a prosaposin receptor agonist useful in alleviating neuropathic pain can be identified by its activity in alleviating neuropathic pain in any of a number of well-established animal models of neuropathic pain (Bennett, supra (1993)). For example, a prosaposin receptor agonist can be identified using an experimental model of peripheral neuropathy produced by segmental spinal nerve ligation in the rat. The Chung rat model duplicates the symptoms of human patients with causalgia, or burning pain due to injury of a peripheral nerve (Kim and Chung, supra (1992)). The surgical procedure of Kim and Chung produces a long-lasting hyperalgesia to noxious heat and mechanical allodynia of the affected foot. As described in EXAMPLE I, rats with spinal nerve ligation according to the procedure developed by Chung and Kim are useful for identifying a prosaposin receptor agonist for use in alleviating neuropathic pain.

A prosaposin receptor agonist useful in alleviating neuropathic pain also can be identified by its activity in alleviating neuropathic pain in a rat model of painful diabetic neuropathy. Hyperalgesia to thermal, mechanical and chemical noxious stimuli also has been reported in diabetic rats with short-term insulin-deficient diabetes induced by selective β cell toxins such as streptozotocin (Calcutt et al., *Pain* 68:293–299 (1996)). Such a rat model is representative of the pain evidenced in diabetic humans, who may exhibit a variety of aberrant sensations including spontaneous pain, pain evoked by light touch and hyperalgesia. Rats treated with streptozotocin or another selective β cell toxin can be treated with a fragment or peptide of interest; subsequently, the response to a noxious stimulus such as 0.5% formalin is measured. A reduced response can be used to identify a prosaposin receptor agonist useful in alleviating neuropathic pain.

A prosaposin receptor agonist useful in alleviating neuropathic pain also can be identified using the neuroma model of Wall et al. This well-recognized model of neuropathic pain reproduces the human symptoms seen following amputation or nerve transection in an intact limb (Wall et al., supra (1979)). As discussed above, a neuroma forms readily after nerve transection due to the frustrated growth of neurite sprouts.

A model of chronic constriction injury also can be used to identify a prosaposin receptor agonist useful in alleviating neuropathic pain. The chronic constriction injury model of Bennett and Xie, supra (1988) is a rat model of peripheral neuropathy that produces pain disorders like those seen in man. In the Bennett model, nerve injury is created by loosely tying constrictive ligatures around the rat sciatic nerve, causing degeneration of nerve distal to the constriction.

Allodynia and hyperalgesia are produced by the constriction injury in addition to spontaneous pain.

Primate models of neuropathic pain also are useful for identifying a prosaposin receptor agonist (see, for example, Lekan et al., supra (1992); Palacek et al., supra (1992)).

As used herein, the term "peptide," as used in reference to an active fragment of prosaposin, a prosaposin-derived peptide or a peptide useful in the methods of the invention, means a compound containing naturally occurring amino acids, non-naturally occurring amino acids or chemically modified amino acids, provided that the compound retains activity in alleviating neuropathic pain or other neurotrophic or myelinotrophic activity as described herein. A prosaposin receptor agonist also can be a peptide mimetic, which is a non-amino acid chemical structure that mimics the structure of a prosaposin-derived peptide and retains activity. Such a mimetic generally is characterized as exhibiting similar physical characteristics such as size, charge or hydrophobicity in the same spatial arrangement found in the prosaposin-derived peptide counterpart. A specific example of a peptide mimetic is a compound in which the amide bond between one or more of the amino acids is replaced, for example, by a carbon-carbon bond or other bond well known in the art (see, for example, Sawyer, *Peptide Based Drug Design*, ACS, Washington (1995)).

As used herein, the term "amino acid" refers to one of the twenty naturally occurring amino acids, including, unless stated otherwise, L-amino acids and D-amino acids. The term amino acid also refers to compounds such as chemically modified amino acids including amino acid analogs, naturally occurring amino acids that are not usually incorporated into proteins such as norleucine, and chemically synthesized compounds having properties known in the art to be characteristic of an amino acid, provided that the compound can be substituted within a peptide such that it retains its biological activity. For example, glutamine can be an amino acid analog of asparagine, provided that it can be substituted within an active fragment of prosaposin that retains its activity in alleviating neuropathic pain or other neurotrophic or myelinotrophic activity as described herein. Other examples of amino acids and amino acids analogs are listed in Gross and Meienhofer, *The Peptides: Analysis, Synthesis, Biology*, Academic Press, Inc., New York (1983). An amino acid also can be an amino acid mimetic, which is a structure that exhibits substantially the same spatial arrangement of functional groups as an amino acid but does not necessarily have both the α-amino and α-carboxyl groups characteristic of an amino acid.

A prosaposin receptor agonist can be isolated or synthesized using methods well known in the art. Such methods include recombinant DNA methods and chemical synthesis methods for production of a peptide. Recombinant methods of producing a peptide through expression of a nucleic acid sequence encoding the peptide in a suitable host cell are well known in the art and are described, for example, in Sambrook et al., *Molecular Cloning: A Laboratory Manual*, 2nd Ed., Vols. 1 to 3, Cold Spring Harbor Laboratory Press, New York (1989).

A prosaposin receptor agonist useful in the invention also can be produced by chemical synthesis, for example, by the solid phase peptide synthesis method of Merrifield et al., *J. Am. Chem. Soc.* 85:2149 (1964). Standard solution methods well known in the art also can be used to synthesize a peptide useful in the invention (see, for example, Bodanszky, *Principles of Peptide Synthesis*, Springer-Verlag, Berlin (1984) and Bodanszky, *Peptide Chemistry*, Springer-Verlag, Berlin (1993)). A newly synthesized peptide can be purified, for example, by high performance liquid chromatography (HPLC), and can be characterized using, for example, mass spectrometry or amino acid sequence analysis.

It is understood that limited modifications can be made to an active fragment of prosaposin without destroying its biological function. Thus, a modification of an active fragment of prosaposin that does not destroy its ability to alleviate neuropathic pain is within the definition of a prosaposin receptor agonist. A modification can include, for example, an addition, deletion, or substitution of amino acid residues; a substitution of a compound that mimics amino acid structure or function; and addition of chemical moieties such as amino or acetyl groups. The activity of a modified peptide in alleviating neuropathic pain can be assayed using an animal model of neuropathic pain, such as those described above or the assay exemplified in EXAMPLE I.

A particularly useful modification of a prosaposin receptor agonist is one that confers, for example, increased stability. For example, incorporation of one or more D-amino acids or substitution or deletion of lysine can increase the stability of an active fragment of prosaposin by protecting against peptide degradation. For example, as disclosed herein, the prosaposin-derived 14-mer SEQ ID NO:2 has an amino acid sequence derived from amino acids 16 to 29 of saposin C but which has been modified by substitution or deletion of each of the three naturally occurring lysines and the addition of a C-terminal tyrosine residue. In particular, the prosaposin-derived 14-mer SEQ ID NO:2 has a D-alanine for lysine substitution at position 2; an alanine for lysine substitution at position 8 and a deletion of lysine at position 11. The D-alanine substitution at position 2 confers increased stability by protecting the peptide from endoprotease degradation, as is well known in the art (see, for example, page 247 of Partridge, *Peptide Drug Delivery to the Brain*, Raven Press, New York (1991)). The substitution or deletion of a lysine residue confers increased resistance to trypsin-like proteases, as is well known in the art (Partridge, supra (1991)). These substitutions increase stability and, thus, bioavailability of peptide SEQ ID NO:2, but do not affect activity in alleviating neuropathic pain.

A useful modification also can be one that promotes peptide passage across the blood-brain barrier, such as a modification that increases lipophilicity or decreases hydrogen bonding. For example, a tyrosine residue added to the C-terminus of the prosaposin-derived peptide (SEQ ID NO:2) increases hydrophobicity and permeability to the blood-brain barrier (see, for example, Banks et al., *Peptides* 13:1289–1294 (1992) and Pardridge, supra (1991)). A chimeric peptide-pharmaceutical that has increased biological stability or increased permeability to the blood-brain barrier, for example, also can be useful in the method of the invention.

One skilled in the art can readily assay the ability of a prosaposin receptor agonist to cross the blood-brain barrier in vivo, for example, as disclosed in EXAMPLE II. In addition, an active fragment of prosaposin can be tested for its ability to cross the blood-brain barrier using an in vitro model of the blood-brain barrier based on a brain microvessel endothelial cell culture system, for example as described in Bowman et al., *Ann. Neurol.* 14:396–402 (1983) or Takahura et al., *Adv. Pharmacol.* 22:137–165 (1992).

As used herein, the term "a neuropathic pain alleviating amount" or "effective amount" means the amount of a prosaposin receptor agonist useful for causing a diminution in neuropathic pain, whether by alleviating neuropathic pain or by inhibiting the onset of neuropathic pain. An effective amount to be administered systemically on a daily basis depends on the body weight of the subject. Preferably, an effective amount to be administered systemically on a daily basis is about 0.1 µg/kg to about 1000 µg/kg. More preferably, an effective amount to be administered systemically on a daily basis is about 10 µg/kg to about 100 µg/kg. An effective amount of a peptide for alleviating or inhibiting the onset of pain can be determined empirically using methods well known to those in the art, including, for example, the assay described in EXAMPLE I or those disclosed above, including assays in primates (Lekan et al., supra (1992), and Palacek et al., supra (1992)).

A typical minimum amount of the peptides of the invention for neurotrophic or myelinotrophic activity in cell growth medium is at least about 5 ng/ml. This amount or more of a peptide of the invention can be used for in vitro use. Typically, concentrations in the range of 0.1 µg/ml to about 10 µg/ml of a peptide of the invention can be used. An effective amount for treatment of a particular tissue can be determined as set forth in EXAMPLES IV and VI.

Neural cells can be treated in vitro or ex vivo by directly administering a peptide of the invention to the cells. This can be done, for example, by culturing the cells in growth medium suitable for a particular cell type, followed by addition of peptide to the medium. When the neural cells to be treated are in vivo, typically in a vertebrate, preferably a mammal, a peptide of the invention can be administered by one of several techniques as described below.

As used herein, the term "subject" means a vertebrate, preferably a mammal and, in particular, a human.

The present invention provides methods of alleviating pain, stimulating neurite outgrowth, inhibiting neural cell death, promoting myelination and inhibiting demyelination and methods of inhibiting sensory or motor neuropathy by administering an effective amount of an active fragment of prosaposin intravenously, intramuscularly, intradermally, subcutaneously, intracranially, intracerebrospinally, topically, orally, transdermally, transmucosally, or intranasally. A pharmaceutically acceptable carrier of well known type can be administered with a prosaposin receptor agonist. Such carriers include, for example, phosphate buffered saline (PBS).

Preferably, an effective amount of a prosaposin receptor agonist is injected directly into the bloodstream of the subject. For example, intravenous injection of a prosaposin receptor agonist can be used to administer the active fragment to the peripheral or central nervous system, since an iodinated prosaposin-derived 18-mer Tyr-Lys-Glu-Val-Thr-Lys-Leu-Ile-Asp-Asn-Asn-Lys-Thr-Glu-Lys-Glu-Ile-Leu (SEQ ID NO:20), consisting of amino acids 12 to 29 of prosaposin-derived 22-mer SEQ ID NO:1 with a substitution of tyrosine for valine at amino acid 12 (MW=2000) crossed the blood-brain barrier and entered the central nervous system as described in EXAMPLE II. The uptake by the brain was approximately 0.03%, which is in the mid-range of values for peptides of that approximate size that will cross the blood-brain barrier (Banks et al., supra (1992)).

Oral administration often can be desirable, provided the prosaposin receptor agonist is modified so as to be stable to gastrointestinal degradation and readily absorbable. The substitution, for example, of one or more D-amino acids can confer increased stability to a prosaposin receptor agonist useful in the invention.

Direct intracranial injection or injection into the cerebrospinal fluid also can be used to introduce an effective amount of a prosaposin receptor agonist into the central nervous system of a subject. In addition, a prosaposin receptor agonist can be administered to peripheral neural tissue by direct injection or local topical application or by systemic administration. Various conventional modes of administration also are contemplated, including intravenous, intramuscular, intradermal, subcutaneous, intracranial, epidural, topical, oral, transdermal, transmucosal, and intranasal administration.

A prosaposin receptor agonist also can be administered in a sustained release form. The sustained release of a prosaposin receptor agonist has the advantage of alleviating neuropathic pain over an extended period of time without the need for repeated administrations of the active fragment.

Sustained release can be achieved, for example, with a sustained release material such as a wafer, an immunobead, a micropump or other material that provides for controlled slow release of the prosaposin receptor agonist. Such controlled release materials are well known in the art and available from commercial sources (Alza Corp., Palo Alto Calif.; Depotech, La Jolla Calif.; see, also, Pardoll, *Ann. Rev. Immunol.* 13:399–415 (1995)). In addition, a bioerodible or biodegradable material that can be formulated with a prosaposin receptor agonist, such as polylactic acid, polygalactic acid, regenerated collagen, multilamellar liposomes or other conventional depot formulations, can be implanted to slowly release the active fragment of prosaposin. The use of infusion pumps, matrix entrapment systems, and transdermal delivery devices also are contemplated in the present invention.

A prosaposin receptor agonist also can be advantageously enclosed in micelles or liposomes. Liposome encapsulation technology is well known. Liposomes can be targeted to a specific tissue, such as neural tissue, through the use of receptors, ligands or antibodies capable of binding the targeted tissue. The preparation of these formulations is well known in the art (see, for example, Pardridge, supra (1991), and Radin and Metz, *Meth Enymol.* 98:613–618 (1983)).

A peptide composition of the invention can be packaged and administered in unit dosage form, such as an injectable composition or local preparation in a dosage amount equivalent to the daily dosage administered to a patient, and if desired can be prepared in a controlled release formulation. Unit dosage form can be, for example, a septum sealed vial containing a daily dose of the active composition of the invention in PBS or in lyophilized form. For treatment of neural diseases, an appropriate daily systemic dosages of a peptide of the invention is based on the body weight of the vertebrate and is in the range of from about 10 to about 100 µg/kg, although dosages from about 0.1 to about 1,000 µg/kg are also contemplated. Thus, for the typical 70 kg human, a systemic dosage can be between about 7 and about 70,000 µg daily and preferably between about 700 and about 7,000 µg daily. A daily dosage of locally administered material will be about an order of magnitude less than the systemic dosage. Oral administration is also contemplated.

The invention also provides a method of alleviating neuropathic pain in a subject by transplanting into the subject a cell genetically modified to express and secrete a prosaposin receptor agonist. Transplantation can provide a continuous source of a prosaposin receptor agonist and, thus, sustained alleviation of neuropathic pain. For a subject suffering from prolonged or chronic neuropathic pain, such a method has the advantage of obviating or reducing the need for repeated administration of an active fragment of prosaposin.

Using methods well known in the art, a cell readily can be transfected with an expression vector containing a nucleic acid encoding an active fragment of prosaposin (Chang, *Somatic Gene Therapy,* CRC Press, Boca Raton (1995)).

Following transplantation into the brain, for example, the transfected cell expresses and secretes an active fragment of prosaposin and, thus, alleviates neuropathic pain. Such a method can be useful to alleviate neuropathic pain as described for the transplantation of cells that secrete substances with analgesic properties (see, for example, Czech and Sagen, *Prog. Neurobiol.* 46:507–529 (1995)).

The cell can be any cell that can survive when transplanted and that can be modified to express and secrete an active fragment of prosaposin. In practice, the cell should be immunologically compatible with the subject. For example, a particularly useful cell is a cell isolated from the subject to be treated, since such a cell is immunologically compatible with the subject.

A cell derived from a source other than the subject to be treated also can be useful if protected from immune rejection using, for example, microencapsulation or immunosuppression. Useful microencapsulation membrane materials include alginate-poly-L-lysine alginate and agarose (see, for example, Goosen, *Fundamentals of Animal Cell Encapsulation and Immobilization* CRC Press, Boca Raton (1993); Tai and Sun, *FASEB J.* 7:1061 (1993); Liu et al., *Hum. Gene Ther.* 4:291 (1993); and Taniguchi et al., *Transplant. Proc.* 24: 2977 (1992)). For example, pain reduction has been achieved using polymer encapsulated cells transplanted into the rat spinal subarachnoid space (Wang et al., *Soc. Neurosci. Abstr.* 17:235 (1991)).

For treatment of a human subject, the cell can be a human cell, although a non-human mammalian cell also can be useful. In particular, a human fibroblast, muscle cell, glial cell, neuronal precursor cell or neuron can be transfected with an expression vector to express and secrete an active fragment of prosaposin such as SEQ ID NO:1. A primary fibroblast can be obtained, for example, from a skin biopsy of the subject to be treated and maintained under standard tissue culture conditions. A primary muscle cell also can be useful for transplantation. Considerations for neural transplantation are described, for example, in Chang, supra (1995).

A cell derived from the central nervous system can be particularly useful for transplantation to the central nervous system since the survival of such a cell is enhanced within its natural environment. A neuronal precursor cell is particularly useful in the method of the invention since a neuronal precursor cell can be grown in culture, transfected with an expression vector and introduced into an individual, where it is integrated. The isolation of neuronal precursor cells, which are capable of proliferating and differentiating into neurons and glial cells, is described in Renfanz et al., *Cell* 66:713–729(1991).

Methods of transfecting cells ex vivo are well known in the art (Kriegler, *Gene Transfer and Expression: A Laboratory Manual,* W. H. Freeman & Co., New York (1990)). For the transfection of a cell that continues to divide such as a fibroblast, muscle cell, glial cell or neuronal precursor cell, a retroviral vector is preferred. For the transfection of an expression vector into a postmitotic cell such as a neuron, a replication-defective herpes simplex virus type 1 (HSV-1) vector is useful (During et al., *Soc. Neurosci. Abstr.* 17:140 (1991); Sable et al., *Soc. Neurosci. Abstr.* 17:570 (1991)).

A nucleic acid encoding an active fragment of prosaposin can be expressed under the control of one of a variety of promoters well known in the art, including a constitutive promoter or inducible promoter. See, for example, Chang, supra (1995). A particularly useful constitutive promoter for high level expression is the Moloney murine leukemia virus long-terminal repeat (MLV-LTR), the cytomegalovirus immediate-early (CMV-IE) or the simian virus 40 early region (SV40).

A nucleic acid sequence encoding an active fragment of prosaposin is disclosed herein. For example, a nucleic acid sequence encoding SEQ ID NO:1 is 5'-TGTGAATTCCTGGTGAAGGAGGTGACCAA GCT-GATTGACAACAACAAGACTGAGA AAGAAATACTC-3' (SEQ ID NO:21) (Dewji et al., *Proc. Natl. Acad. Sci. USA* 84:8652–8656 (1987)). In order to direct secretion of peptide SEQ ID NO:1, for example, a nucleic acid encoding a signal sequence, such as the signal sequence of β-lactamase, can be operably linked to SEQ ID NO:21 as described in Simon et al., *J. Cell Biol.* 104:1165 (1987).

The invention further provides a method of inhibiting the onset of neuropathic pain in a subject by administering an effective amount of a prosaposin receptor agonist to the subject. The method of preventing neuropathic pain is useful when applied prior to a painful event, for example, prior to chemotherapy or surgery that is known to result in neuropathic pain.

The following examples are intended to illustrate but not limit the present invention.

EXAMPLE I

Alleviation of Neuropathic Pain in Chung Model Rats

This EXAMPLE describes the effects of bolus intrathecal injection of an active fragment of prosaposin in the Chung experimental model of peripheral neuropathic pain.

Each of the three peptides were obtained in pure form by chemical synthesis, dissolved in sterile PBS and buffered to a neutral pH.

The surgical procedure previously described by Kim and Chung, supra (1992) was performed on male Sprague-Dawley rats weighing 120 to 150 grams to induce an allodynic state. Briefly, the rats were anesthetized with halothane; subsequently, the left L-5 and L-6 spinal nerves were isolated adjacent to the vertebral column and ligated with 6.0 silk suture distal to the dorsal root ganglion.

After a ten to fourteen day post operative recovery period, a spinal catheter was introduced. Five days following the second surgery, intrathecal drug administration was accomplished using a gear driven micro-injection syringe connected to a spinal catheter inserted through the foramen magnum. Prior to testing, the rats were placed in clear plastic wire meshed cages and allowed to acclimate.

To assess the 50% mechanical threshold for paw withdrawal, a von Frey hair was applied to the hind foot avoiding the foot pad. Each of the von Frey hairs, which are calibrated to bend at increasing log forces, were pressed perpendicularly to the foot with sufficient force to cause slight bending for a duration of approximately six to eight seconds. A positive response was noted if the foot was sharply withdrawn. Six data points were collected for each point with the maximum and minimum stimulus noted for each time point. The resulting pattern of the responses was tabulated, and the 50% response threshold was computed. The graph gives the response to the indicated dosage of peptide given as a single intrathecal bolus injection. The X-axis indicates the time after the injection at which point the hypersensitivity to pressure on the foot pad was measured.

A All surgically lesioned rats showed tactile allodynia prior to injection with an active fragment of prosaposin. As shown at time zero in FIG. 1, the measured threshold was less than 3.0 to 4.0 g in the absence of peptide. Intrathecal injection of 0.7 or 0.07 µg of the prosaposin-derived 22-mer peptide (SEQ ID NO:1) suppressed allodynia in a dose-dependent fashion. The reduction of allodynia is manifest by the increase in the force threshold as the rats withstand an increasing force before withdrawing the affected foot.

A significant effect was observed by 15 minutes after the injection. The maximum effect was seen 120 minutes post-injection. Rats injected with the highest dose of the prosaposin-derived 22-mer peptide (SEQ ID NO:1) continued to demonstrate significantly reduced allodynia at the latest time point assayed (180 minutes). Rats that were injected with 0.007 µg prosaposin-derived 22-mer peptide (SEQ ID NO:1) showed no significant reduction in allodynia. No significant side effects such as sedation were observed at any concentration.

Figure 2:
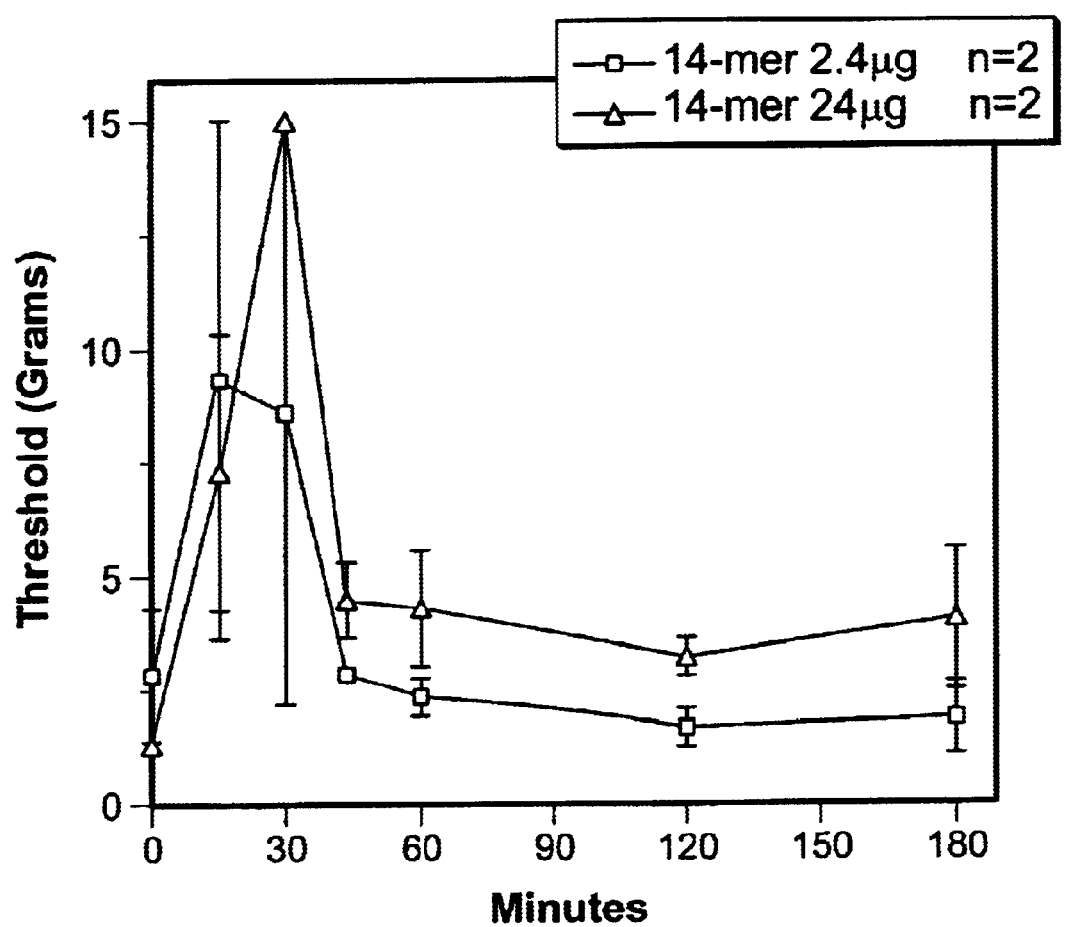
FIG. 2 shows the threshold of tactile allodynia before (time 0) and at various times after bolus injection of prosaposin-derived 14-mer peptide (SEQ ID NO:2) in Chung model rats.

The ability of the prosaposin-derived 14-mer peptide (SEQ ID NO:2; see TABLE 1) to relieve allodynia in Chung model rats also was examined. As shown in FIG. 2, the active fragment of prosaposin (SEQ ID NO:2) was effective in reducing allodynia. The peak effect of the prosaposin-derived 14-mer peptide (SEQ D NO:2) was observed 15 to 30 minutes following the injection and returned to the pre-injection value by 60 minutes (FIG. 2). No side effects were observed at either concentration of prosaposin-derived 14-mer peptide (SEQ ID NO:2) tested.

A mutant 22-mer peptide (SEQ ID NO:8) that differs from the prosaposin-derived 22-mer peptide (SEQ ID NO:1) by containing an aspartic acid residue instead of an asparagine (see TABLE 4) also was tested for activity in relieving allodynia in Chung model rats. No change in the allodynic response of the Chung rats was observed following injection of 17.5 µg mutant 22-mer peptide (SEQ ID NO:8).

Normal rats, which do not experience pain as a result of surgical lesion introduced according to the Chung model, also were injected with an active fragment of prosaposin (SEQ ID NO:1) and tested for their response to a heat stimulus according to the procedure developed by Bennett and Xie, supra (1988). Briefly, the period of time before the rat withdraws the affected foot from a source of heat is defined as the hot plate latency and is a measure of tolerance to pain caused by a heat stimulus.

An intrathecal catheter was placed into normal male Sprague Dawley rats. Five days after this surgery, rats were injected intrathecally with an active fragment of prosaposin (SEQ ID NO:1). Rats were examined on the hot plate (52.5° C.); hot plate response latencies were measured prior to injection and at various time points up to 180 minutes after the injection. No significant elevation of the hot plate response latency was observed. Thus, the prosaposin-derived peptide SEQ ID NO:1 does not effect the perception of pain in normal animals.

EXAMPLE II

In vivo Uptake of Prosaposin-derived Peptides by the Central Nervous System

The results described in this EXAMPLE indicate that prosaposin-derived peptides cross the blood-brain barrier.

An 18-mer peptide (SEQ ID NO:20) consisting of amino acids 12–29 of saposin C with a tyrosine substituted for valine at position 12 was chemically synthesized on an Applied Biosystems Model 430 peptide synthesizer. The peptide was then radioiodinated by the lactoperoxidase method; $20 \times 10^6$ cpm radiolabeled peptide were injected into the auricles of rats. The animals were sacrificed after one hour and 24 hours, and the hearts were perfused with isotonic saline in order to remove the blood from the brain.

In order to determine the percentage of peptide uptake, the brain was then counted in a gamma counter. In addition, the brain was homogenized and fractionated into a capillary rich fraction (pellet) and a parenchymal brain fraction (supernatant) after dextran centrifugation (Triguero et al., *J. Neurochem.*, 54:1882–1888 (1990)). This method allows for the discrimination between radiolabeled peptide within blood vessels, and that within the brain. After 24 hours, 0.017% of the injected peptide (SEQ ID NO:20) was detected in whole brain; 75% of the label was in the parenchymal fraction and 25% was in the capillary fraction. At 1 hour, 0.03% of the injected dose was present in whole brain.

The prosaposin-derived peptide SEQ ID NO:2 also was assayed for ability to cross the blood-brain barrier as follows. A female Sprague-Dawley rat was anesthesized with methoxyflurane, and approximately 20 µg peptide SEQ ID NO:2 ($3.2 \times 10^8$ cpm) was injected into the tail vein. After 40 minutes, the rat was sacrificed by ether anesthesia and perfused with about 250 ml PBS through the heart. The total amount of peptide in brain, liver and blood was calculated as a percentage of the injected material as shown in TABLE 6. In order to determine the localization in brain, the capillary depletion method of Triguero, *J. Neurochem.* 54:1882 (1990) was used to separate brain tissue into a parenchyma fraction and a brain capillary fraction. The fractionation results showed that 87% of the SEQ ID NO:2 peptide present in brain was localized to brain parenchyma while 13% was found in brain capillary.

TABLE 6

| TISSUE | WEIGHT | TOTAL CPM IN TISSUE | PERCENTAGE OF INITIAL CPM |
| --- | --- | --- | --- |
| Brain | 1.3 gm | 161,000 | 0.050 |
| Liver | 8.8 gm | $5.2 \times 10^6$ | 1.625 |
| Blood | about 22 µl | $1.01 \times 10^8$ | 31.6 |

In a similar experiment in which rats were sacrificed after three hours treatment with SEQ ID NO:2, 0.06% of the peptide was evident in brain, of which 85% was in the parenchyma. These results demonstrate that at least some of the prosaposin-derived peptide SEQ ID NO:2 crossed the blood brain barrier and was concentrated in the brain parenchyma rather than the vascular endothelium (blood vessels). The percentage of peptide which crossed the blood brain barrier is in the mid-range of peptides which cross the barrier as set forth in Banks, supra (1992).

In order to determine the percentage of intact material in the brain, liver and blood, radiolabeled material (SEQ ID NO:2) isolated from the tissues was analyzed by high pressure liquid chromatography. To normalize for degradation during processing of tissue homogenates, peptide SEQ ID NO:2 was added to tissue homogenates. The extent of degradation observed with the added peptide material was used to normalize for degradation during tissue processing. After normalization, the results were as follows: SEQ ID NO:2 was about 60% intact in brain; about 80% intact in liver and about 40% intact in blood. In a second experiment, peptide SEQ ID NO:2 was about 68% intact in brain. These results indicate that the peptide SEQ ID NO:2 crosses the blood brain barrier and is largely intact in brain.

EXAMPLE III

Alleviation of Neuropathic Pain in Diabetic Rats

This EXAMPLE describes the effects of intraperitoneal administration of a peptide having the sequence of SEQ ID NO:2 in a rat model of diabetic neuropathy.

Rats were made diabetic by a single intraperitoneal injection of streptozotocin (STZ) (50 mg/kg body weight, freshly dissolved in 0.9% sterile saline) to ablate pancreatic β cells and induce insulin deficiency as described in Calcutt et al., *Pain* 68:293–299 (1996). Two days later, diabetes was confirmed in streptozotocin-injected rats by measuring blood glucose levels. Streptozotocin-injected animals with a blood glucose concentration below 15 mmol/l were excluded from subsequent studies, according to the commonly accepted definition of non-fasting hyperglycemia in studies of diabetes in rats.

Both diabetic and control rats were studied at 8 weeks by analyzing the behavioral response to the noxious chemical formalin as an indicator of allodynia (Calcutt et al. supra (1996)). Briefly, rats received a subcutaneous injection of freshly-prepared formalin (50 μl of 0.5% solution in sterile saline) into the dorsal surface of the right hind paw. This concentration of formalin induces sub-maximal behavioral responses in control rats and allows detection of hyperalgesia in diabetic rats during phases Q and 2 (Calcutt et al., *Eur. J. Pharmacol.* 285:189–197 (1995). Animals were transferred to an observation chamber constructed to allow continuous visualization of the paws. The number of flinches during one minute periods were counted at 5 minute intervals for the next 60 minutes by an observer who was unaware of the treatment group of each animal. Phase 1 was defined as the initial measurement of flinching (1–2 and 5–6 minutes post injection); the Q (quiescent) phase as the measurements made at 10–11, 15–16 and 20–21 minutes; and Phase 2 as all subsequent measurements post injection, as previously defined for studies of diabetic rats (see, for example, Malmberg et al., *Neurosci. Lett.* 161:45–48 (1993)). Comparisons of activity during each phase were made by summing the flinches at measurement points within the phase. Diabetic rats gave an abnormal flinch response, as has been reported previously.

Figure 3:
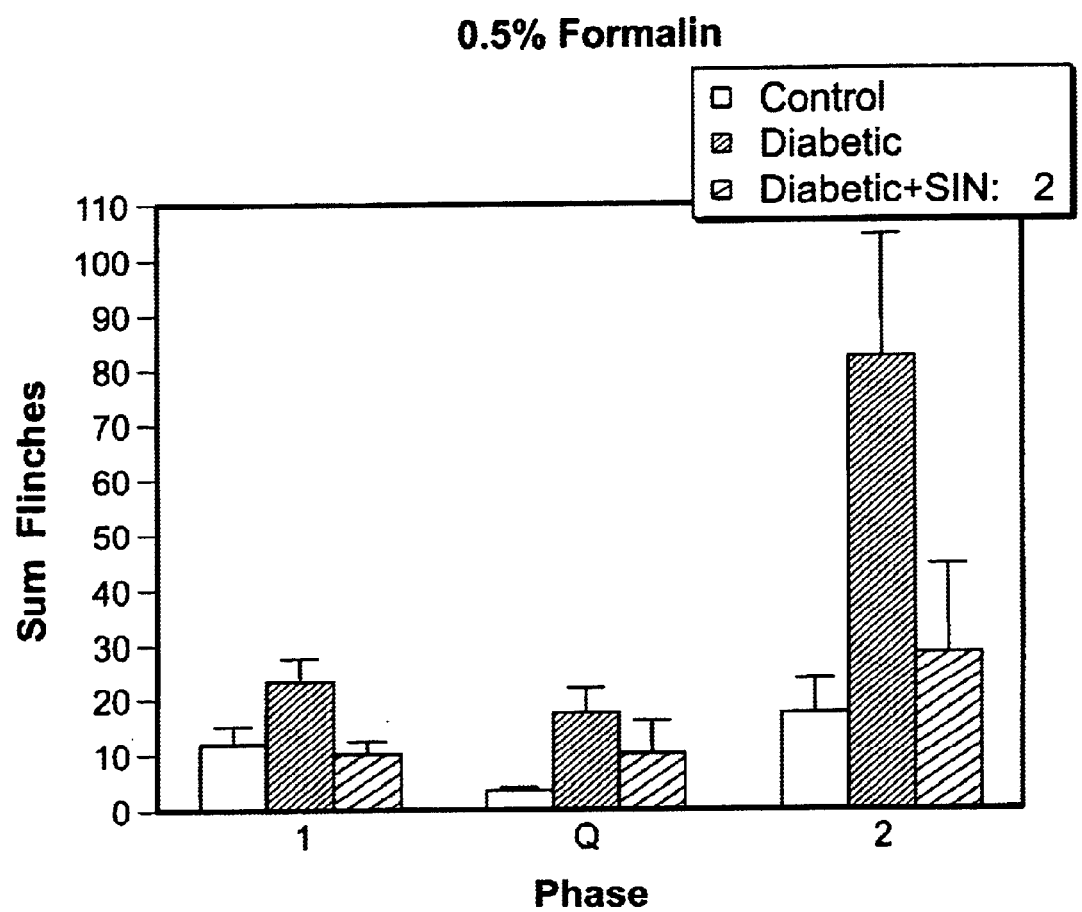
FIG. 3 shows the sum flinches in response to 0.5% formalin after intraperitoneal administration of prosaposin-derived 14-mer peptide (SEQ ID NO:2) or saline in diabetic rats.

Peptide SEQ ID NO:2 was obtained in pure form by chemical synthesis, dissolved in sterile PBS and buffered to a neutral pH. Diabetic rats were divided in two groups of four animals each, which were administered saline or peptide SEQ ID NO:2, respectively. Two hours before treatment with 0.5% formalin, the diabetic rats were treated with saline or 200 μg/kg peptide SEQ ID NO:2 using intraperitoneal administration. As shown in FIG. 3, administration of SEQ ID NO:2 completely prevented the abnormal flinch response in Phase 1 and ameliorated the response in Phase 2 by 70%. Thus, parenteral administration of peptide SEQ ID NO:2 alleviated the pain from formalin injection in a rat model of painful diabetic neuropathy.

EXAMPLE IV

Stimulation of Neurite Outgrowth in vitro

This EXAMPLE describes the use of a peptide having the sequence of SEQ ID NO:2 in stimulating neurite outgrowth in vitro.

NS20Y neuroblastoma cells are grown in Dulbecco's modified Eagle medium (DMEM) containing 10% fetal calf serum (FCS). Cells are removed with trypsin and plated in 30 mm petri dishes onto glass coverslips. After 20 to 24 hours, the medium is replaced with 2 ml DMEM containing 0.5% fetal calf serum with 0, 0.5, 1, 2, 4 or 8 ng/ml of a peptide having sequence SEQ ID NO:2 or a scrambled control peptide. Cells are cultured for an additional 24 hours, washed with PBS and fixed with Bouin's solution (saturated aqueous picric acid/formalin/acetic acid 15:5:1) for 30 minutes. After fixative is removed with PBS, neurite outgrowth is scored under a phase contrast microscope. Cells exhibiting one or more clearly defined neurites equal to or longer than one cell diameter are scored as positive for neurite outgrowth. At least 200 cells are scored in different positions of each dish to determine the percentage of neurite bearing cells with each peptide assayed in duplicate.

The peptide shown in SEQ ID NO:2 significantly increases neurite outgrowth in NS20Y cells as compared to a scrambled control peptide having the same amino acids in a different order. Increased neurite outgrowth is evident using as little as 0.5 ng/ml peptide.

EXAMPLE V

Inhibition of Neural Cell Death in vitro

This EXAMPLE describes the use of a peptide having the sequence of SEQ ID NO:2 in inhibiting neural cell death in vitro.

NS20Y cells are plated as described in EXAMPLE IV and grown on glass coverslips in 0.5% fetal bovine serum for 2 days in the presence or absence of 8 ng/ml of a peptide having the sequence shown as SEQ ID NO:2 or a scrambled control peptide. Media is removed and 0.2% trypan blue in PBS is added to each well. Dead cells stain blue with the trypan blue dye and are scored as a percentage of the total on an inverted microscope, counting 400 cells in four areas of each well. The average error of duplicates is ±5%. The peptide shown as SEQ ID NO:2 substantially reduces the number of trypan blue-positive (dead) cells. This indicates that a peptide having the sequence SEQ ID NO:2 can inhibit programmed cell death.

EXAMPLE VI

Ex vivo Myelination Assay

This EXAMPLE describes the use of a peptide having the sequence of SEQ ID NO:2 in stimulating neurite outgrowth ex vivo and in promoting myelination.

Newborn mouse cerebellar explants are prepared according to Satomi, *Zool. Sci.* 9:127–137 (1992). Neurite outgrowth and myelination are observed over 22 days in culture, during the period when the newborn mouse cerebellum normally undergoes neuronal differentiation and myelination begins. On the second day after preparation of the explants, the peptide having the sequence of SEQ ID NO:2 is added to three explants at a concentration of 10 μg/ml and a scrambled control peptide is added to three explants at a concentration of 10 μg/ml. Neurite outgrowth and myelination in three control and three treated explants is assessed under a bright field microscope with a video camera. On the eighth day, cultures containing the peptides are thinner and more spread out than control cultures. On day 15, cultures treated with peptide SEQ ID NO:2 contain many cells with long projections at the periphery of the explant. Such projections are absent or less prominent in control cultures. Cultures treated with peptide SEQ ID NO:2 contain significantly more myelinated axons in the subcortical white matter at 22 days compared to control explants. Thus, the peptide of the invention induces myelination in differentiating cerebellum ex vivo.

EXAMPLE VII

Inhibition of Demyelination

Reduction of Schwann cell death is correlated with inhibition of demyelination. Schwann cells contain an extensive myelin sheath. The addition of the peptide shown in SEQ ID NO:2 to Schwann cells in culture reduces Schwann cell death in a dose-dependent manner not seen with a control scrambled peptide. Thus, a peptide of the invention having the sequence of SEQ ID NO:2 can inhibit demyelination.

EXAMPLE VIII

Treatment of Traumatic Ischemic CNS Lesions

Humans with traumatic lesions to the spinal cord receive an intracerebrospinal injection or direct injection of about 100 µg/ml of the peptide shown in SEQ ID NO:2 in a sterile saline solution or in depot form to enable slow, continuous release of the peptide at the lesion site. Improvement is assessed by gain of motor nerve function such as increased limb movement. Treatments are repeated until no further improvement occurs.

EXAMPLE IX

Treatment of Demyelination Disorders

Patients diagnosed with early stage MS are given a peptide having the sequence shown in SEQ ID NO:2 by direct intravenous injection into the cerebrospinal fluid using the same dose range as in EXAMPLE VIII. Dosages are repeated daily or weekly and improvement in muscle strength, musculoskeletal coordination and myelination (as determined by magnetic resonance imaging (MRI)) is observed.

EXAMPLE X

Treatment of Sensory Neuropathy

Mice were administered taxol in order to induce sensory neuropathy. The taxol-treated mice were administered 100 µg/kg, 200 µg/kg or 1 mg/kg of the prosaposin-derived peptide SEQ ID NO:2.

The loss of thermal sensation was measured using a Hargreaves sensory testing apparatus as an indicator of sensory neuropathy. Each of the three doses of peptide SEQ ID NO:2 administered were effective in inhibiting loss of thermal sensation in taxol-treated mice. The prosaposin-derived 22-mer peptide SEQ ID NO:1 also was similarly assayed and found to be effective in inhibiting less of thermal sensation in the taxol-treated mice. These results show that prosaposin-derived peptides such as SEQ ID NO:1 and SEQ ID NO:2 can be used to effectively inhibit sensory neuropathy.

EXAMPLE XI

Incorporation of $^{32}$P into NS20Y Proteins After Treatment with Prosaposin or its Active Fragments NS20Y cells were incubated in phosphate-free Hanks' balanced salt solution containing 2.5 µg/ml actinomycin D and 80–100 µCi/ml carrier-free [$^{32}$P]-orthophosphate (New England Nuclear) and effector proteins (0.5–1.0 µg/ml) and incubated for 10–15 minutes at room temperature. Cells were solubilized in SDS-PAGE sample buffer, analyzed by SDS-PAGE and autoradiographed.

Prosaposin and saposin C were found to stimulate phosphorylation of proteins of 148, 100, 80, 68, 50, 38 and 34 kDa to a greater extent than controls or cells treated with similar concentrations of saposins A, B or D. This 148 kDa protein may be phospholipase C-γ, a protein known to be involved in phospholipid metabolism and which is phosphorylated on tyrosine residues in response to a number of growth factors. Densitometric analysis indicated a 3–5 fold stimulation of phosphorylation after 10 minutes. Treatment of gels with alkali revealed that the prominent phosphorylated proteins were alkali-resistant, indicating that they contain phosphotyrosine and/or phosphothreonine (located next to proline) residues. These results indicate that prosaposin and its active fragments bind to a cell surface receptor and activate a kinase cascade, similar to other neurotrophins and growth factors. Since prosaposin-ganglioside $GM_1$ or saposin C-ganglioside $GM_3$ complexes inhibit neuritogenesis, while prosaposin or saposin C alone promote this process, this indicates that gangliosides may abolish neurotogenic activity by masking a receptor binding site on the neurotrophin. In addition, since prosaposin and its active fragments induce tyrosine phosphorylation of cytoplasmic proteins in responsive cells, most likely by activation of a tyrosine kinase similar to cytokines and growth factors, this provides further evidence that a cell surface receptor is involved.

A 20 kDa protein has been identified as the putative receptor for prosaposin as described in the following EXAMPLE:

EXAMPLE XII

Isolation of a Putative Prosaposin Receptor

A putative prosaposin receptor protein was isolated from whole rat brain, rat cerebellum and mouse neuroblastoma cells using the plasma membrane P-100 fraction. Briefly, cells or tissues were solubilized and centrifuged at 14,000 rpm to remove debris. The supernatant was centrifuged at 40,000 rpm for 1 hour at 4° C. The pellet, enriched in plasma membrane, was solubilized in RIPA buffer (10 mM MOPS, pH 7.5, 0.3 M sucrose, 5 mM EDTA, 1% Trasylol, 10 µM leupeptin and 10 µM antipain). This P-100 fraction was applied to an affinity column containing the bound, active 22-mer fragment of saposin C. The column was washed with 0.05 M NaCl to elute loosely-bound proteins followed by 0.25 M NaCl which eluted the putative 54–60 kDa prosaposin receptor. In addition, it was determined that the 54–60 kDa protein could be eluted using a 100-fold excess of unbound peptide thus demonstrating specific elution. The 54–60 kDa protein was approximately 90% pure as judged by SDS-PAGE. The protein was purified to homogeneity using HPLC and eluted at 50% acetonitrile in an acetonitrile/water gradient on a Vydac C4 column. After treatment with the cross-linking reagent disuccinimidyl suberate (DSS; Pierce, Rockford, Ill.), the 54–60 kDa protein bound irreversibly to $^{125}$I labeled saposin C as evidenced by the 72 kDa molecular weight of the complex (60 kDa+12 kDa).

EXAMPLE XIII

Alleviation of Neuropathic Pain in Selzer Model Rats

Prosaptide TX 14(A) (SEQ ID NO:2) was tested for relief of hyperalgesia in the Selzer rat model. After induction of hyperalgesia by ligation of the sciatic nerve in one hind limb, the animals were injected with Prosaptide TX 14(A). Relief was measured using the hot plate withdrawal technique comparing ligated vs. unligated hind foot withdrawal. Within 3 hours of injection of Prosaptide TX 14(A), intravenous at a dose of 200 mg/kg, nearly complete relief of hyperalgesia was observed. The relief lasted for up to 48 hours post injection.

EXAMPLE XIV

The Effects of Prosaptide TX 14(A) on the Relief of Neuropathy in a Diabetic Rat Model While conventional medical treatment of diabetes mellitus markedly prolongs life-span, serious medical complications affect a large proportion of the more than 10 million people believed to have diabetes in the USA. Peripheral neuropathy is the most common complication, affecting one third of newly diagnosed cases. The frequency of neuropathy increases with duration of disease to affect over half of all diabetics. Nerve dysfunction usually progresses to become a distal symmetrical polyneuropathy with morphologic evidence of paranodal widening, segmental demyelination and remyelination, axonal atrophy and ultimate fiber loss. This pathology is accompanies by loss of sensory function that, when coupled with impaired healing processes and vascular disease, can lead to gangrene and limb amputation.

Hyperglycemia may be induced in animals by a variety of means and diabetic rodents have been widely studied to gain insights into mechanisms underlying diabetic complications. Acute, insulin-deficient, experimental diabetes may be introduced by selective chemical ablation of the beta cells of the pancreas using streptozatocm (STZ) to produce analogous to severe type 1 (insulin-dependent) diabetes.

STZ-diabetic rats exhibit electrophysiologic disorders that are similar to those found in newly-diagnosed diabetic patients. Symptoms include, reduced nerve conduction, relacitios, and resistance to ischemic conduction block. Other functional disorders present in the peripheral nerves of STZ-diabetic rats include exaggerated pain responses to a painful stimulus with concurrent thermal hypoalgesia (slowing of response times to painful thermal stimuli, reduced levels of neuropeptide neurotransmitters, impaired regeneration after injury and reduced nerve blood).

Figure 4A:
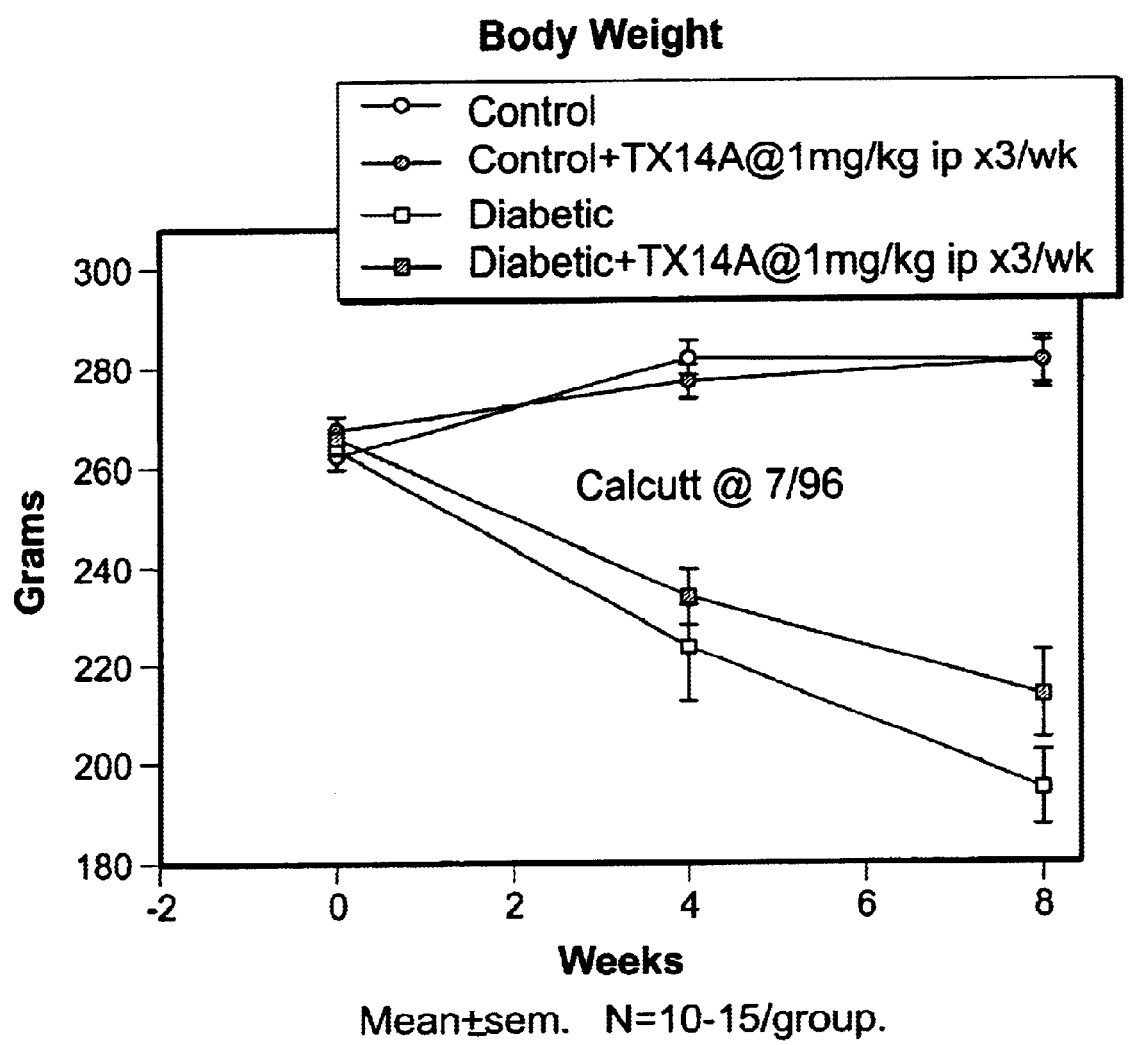
FIG. 4 shows the effects of prosaptide TX 14(A) on the relief of neuropathy in a diabetic rat model. Prosaptide TX 14(A) prevented hypoalgesia in streptozotocin (STZ)-diabetic rats
Figure 4B:
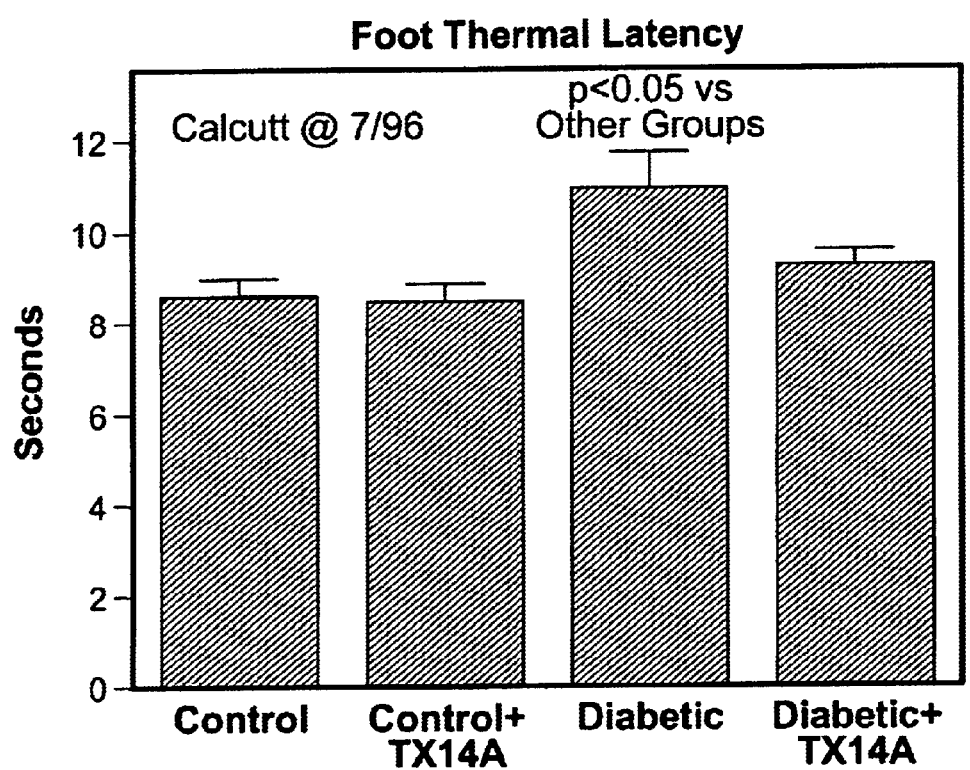

Since prosaposin and the prosaptides have been shown to cause peripheral and central nerve regeneration and prevent demyelination and induce remyelination, this preliminary EXAMPLE was conducted using prosaptide TX 14(A) (SEQ ID NO:2) using STZ-diabetic rats. Control and STZ-diabetic rats were treated using 1000 μg prosaptide TX 14(A) per kg body weights i.p., three times per week for 8 weeks. Treatment did not prevent hyperglycemia or loss of body weight in diabetic rats (control=280 gm; control plus prosaptide TX 14(A)=280 gm; diabetic=195 gm; and diabetic plus prosaptide TX 14(A)=204 gm). However, prosaptide TX 14(A) prevented hypoalgesia in the STZ-diabetic rats (FIG. 4).

This is an important finding as loss of thermal sensation and thermal pain sensation is an early indicator of neuropathy in diabetic patients.

EXAMPLE XV

Figure 5A:
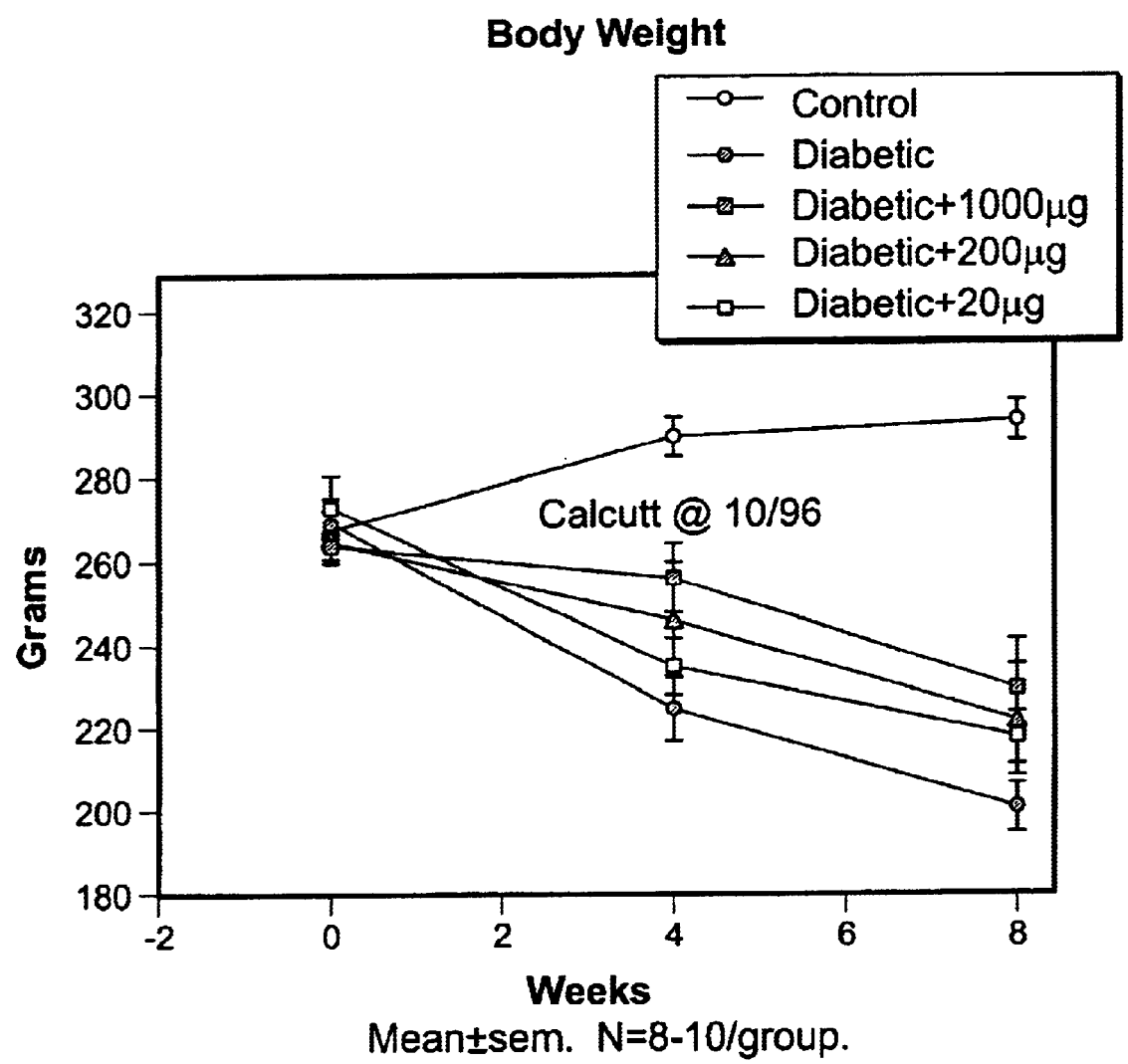
FIG. 5 shows the effects of diabetes and efficacy of a peptide fragment of prosaposin in treating diabetic nerve dysfunction. All three groups treated with prosaptide TX 14(A) showed significant decreases in weight loss in a dose dependent manner when compared to diabetic animals. Thermal response latency was restored to control non-diabetic levels in animals treated with 200 and 1000 $\mu$g prosaptide TX 14(A), while the 20 $\mu$g treatment group showed an intermediate response.
Figure 5B:
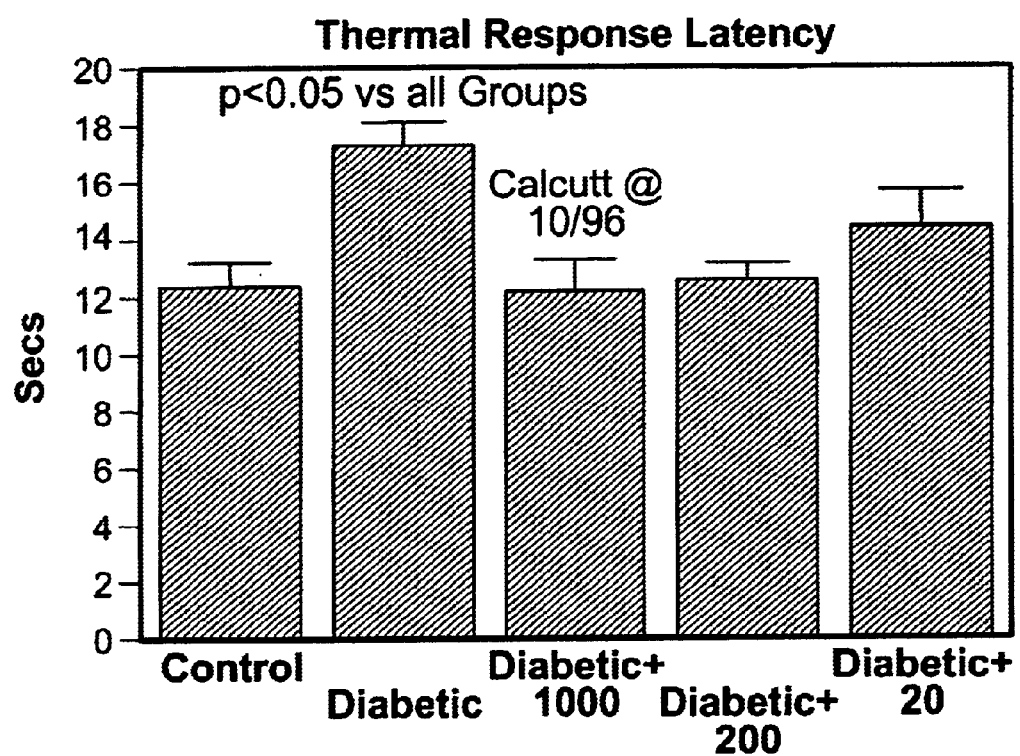
Figure 6A:
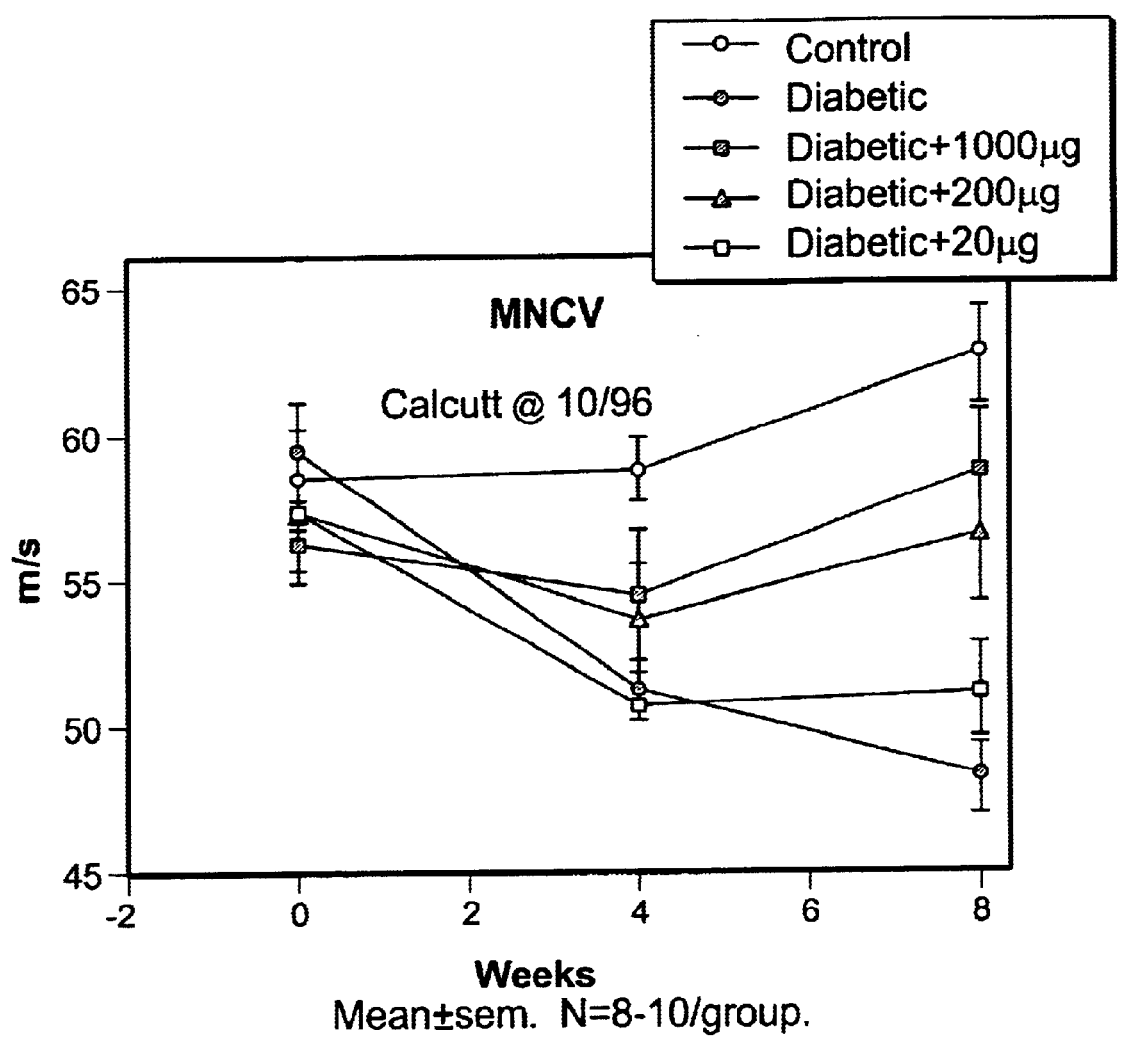
FIG. 6 shows the effects of diabetes and efficacy of a peptide fragment of prosaposin in treating diabetic nerve dysfunction. Diabetic animals treated with prosaptide TX 14(A) at doses of 200 and 1000 $\mu$g/kg body weight showed enhanced motor nerve conduction velocities compared to the untreated diabetic group and diabetic animals receiving 20 $\mu$g/kg body weight. In addition, all prosaptide TX 14(A)-treated rats showed a slower loss of sensory nerve conduction velocity when compared to diabetic unheated animals.
Figure 6B:
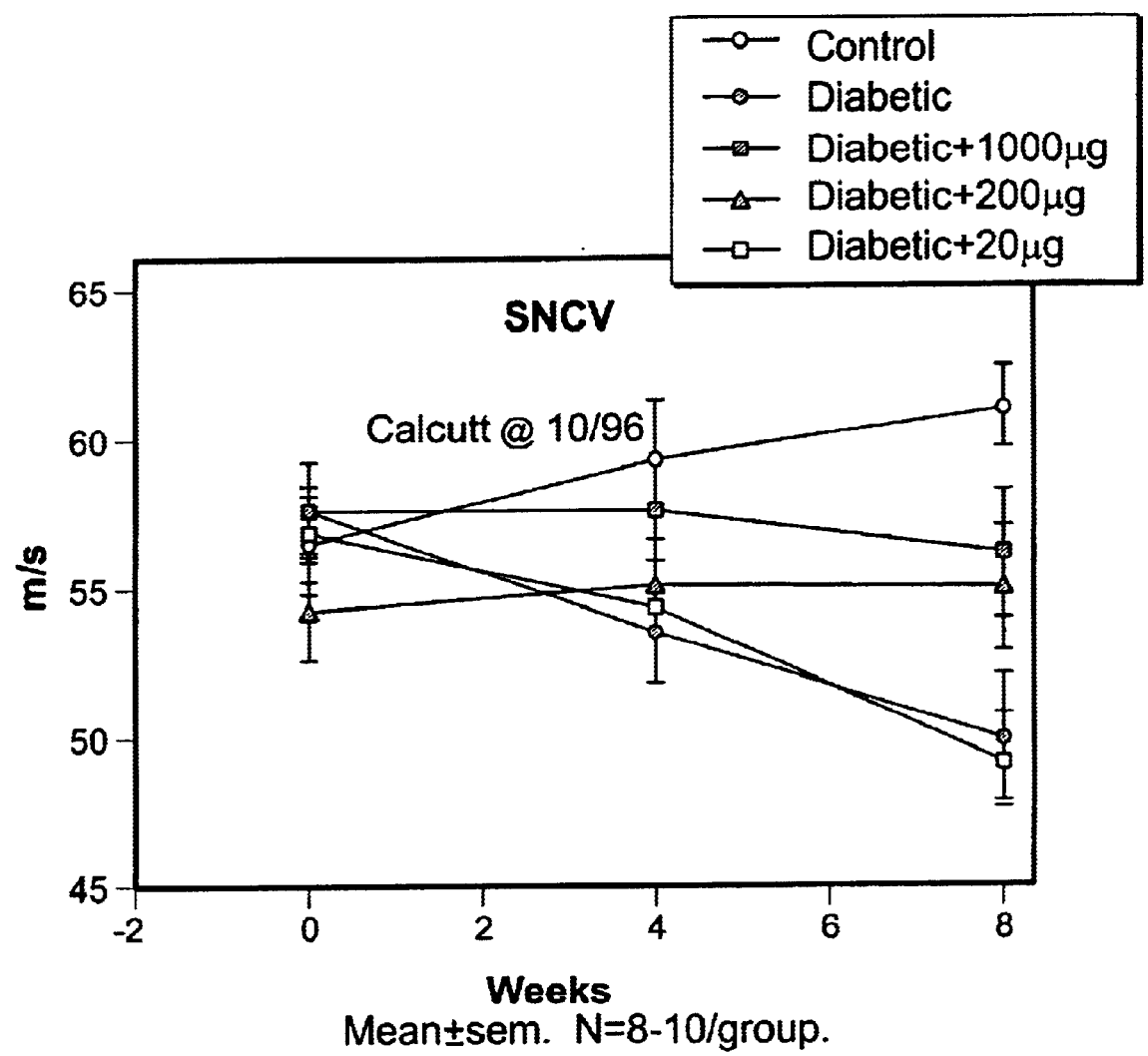

Prosaposin in Peripheral Nerve: Effects of Diabetes and Efficacy of a Peptide Fragment of Prosaposin in Treating Diabetic Nerve Dysfunction A more comprehensive EXAMPLE was then undertaken to include more parameters and to establish a dose response of prosaptide TX 14(A) (SEQ ID NO:2). In this EXAMPLE, control and STZ-diabetic rats were treated with prosaptide TX 14(A) at doses of 20 μg/kg, 200 μg/kg, and 1000 μg/kg body weight, i.p., three times per week for 8 weeks. The rats were weighed at the beginning, midpoint and the end of the experiment and motor nerve conduction (MNCV) and sensor nerve conduction velocity (SNCV) measurements were taken at the three time points. In this EXAMPLE, all three groups treated with prosaptide TX 14(A) showed significant decreases in weight loss in a dose dependent manner when compared to diabetic animals (FIG. 5). Thermal response latency was restored to control non-diabetic levels in animals treated with 200 and 1000 μg prosaptide TX 14(A), while the 20 μg treatment group showed an intermediate response (FIG. 5). Diabetic animals treated with prosaptide TX 14(A) at doses of 200 and 1000 μg/kg body weight showed enhanced motor nerve conduction velocities compared to the untreated diabetic group and diabetic animals receiving 20 μg/kg body weight (FIG. 6). In addition, all prosaptide TX 14(A)-treated rats showed a slower loss of sensory nerve conduction velocity when compared to diabetic unheated animals (FIG. 6).

In detail, the results of this EXAMPLE were as follows: Saposin C and its precursor prosaposin exhibit neurogenic properties and protect neurons from ischemic injury. Immunostaining, using a monoclonal antibody that recognizes both prosaposin and saposin C, was demonstrated in Schwann cells of peripheral nerve. Further, after 8 weeks of untreated diabetes, prosaposin mRNA levels increased 2-fold in the peripheral nerves of rats, suggesting either dysfunctional processing or a local response to developing neuropathy. Therefore, the effect of a 14 amino acid neuroactive peptide fragment of saposin C (prosaptide; SEQ ID NO:2) on peripheral nerve function in control and diabetic rats was investigated. MNCV (63.7±1.0 m/s;: mean term) and SNCV (63.4±1.3) were significantly ($p<0.05$ or less by ANOVA and Student-Newman-Keuls test) reduced after 8 weeks of streptozotocin diabetes (52.8±1.1 and 49.8±1.8 respectively). These deficits were attenuated by thrice weekly treatment (1 mg/kg i.p. for 8 weeks) with prosaptide (58.1±1.2 and 54.9±1.3 respectively). Thermal hypoalgesia in diabetic rats (control=85±3.4 sec: diabetic=11.0±0.8) was also prevented by prosaptide treatment (8.8±0.6) while there was no effect on hyperglycemia, accumulation of polyol pathway metabolites, nerve myo-inositol depletion or reduced nerve laser Doppler flux. There was no detectable effect of prosaptide on any measured parameter in control rats. In a subsequent time course study, thermal hypoalgesia and the decline in nerve conduction velocities during 8 weeks of diabetes were attenuated by prosaptide in a dose-dependent manner using thrice weekly treatment with either 20,. 200 or 1000 μg i.p. These data demonstrate the novel presence in Schwann cells of a neuroactive protein (prosaposin) whose mRNA is increased during diabetes. Moreover, a peptide fragment of this protein (prosaptide; SEQ ID NO:2) is capable of preventing slowed nerve conductance and thermal hypoalgesia in diabetic rats without modulating exaggerated polyol pathway flux or reduced nerve vascular perfusion.

This EXAMPLE demonstrates that prosaptide TX 14(A) (SEQ ID NO:2) can prevent the symptoms of diabetic neuropathy and slow or prevent motor and sensory nerve degeneration as measured by nerve conduction velocities. In addition, the optimal dose of prosaptide can now be established as greater than 20 μg/kg and less than 100 μg/kg body weight.

EXAMPLE XVI

Figure 7:
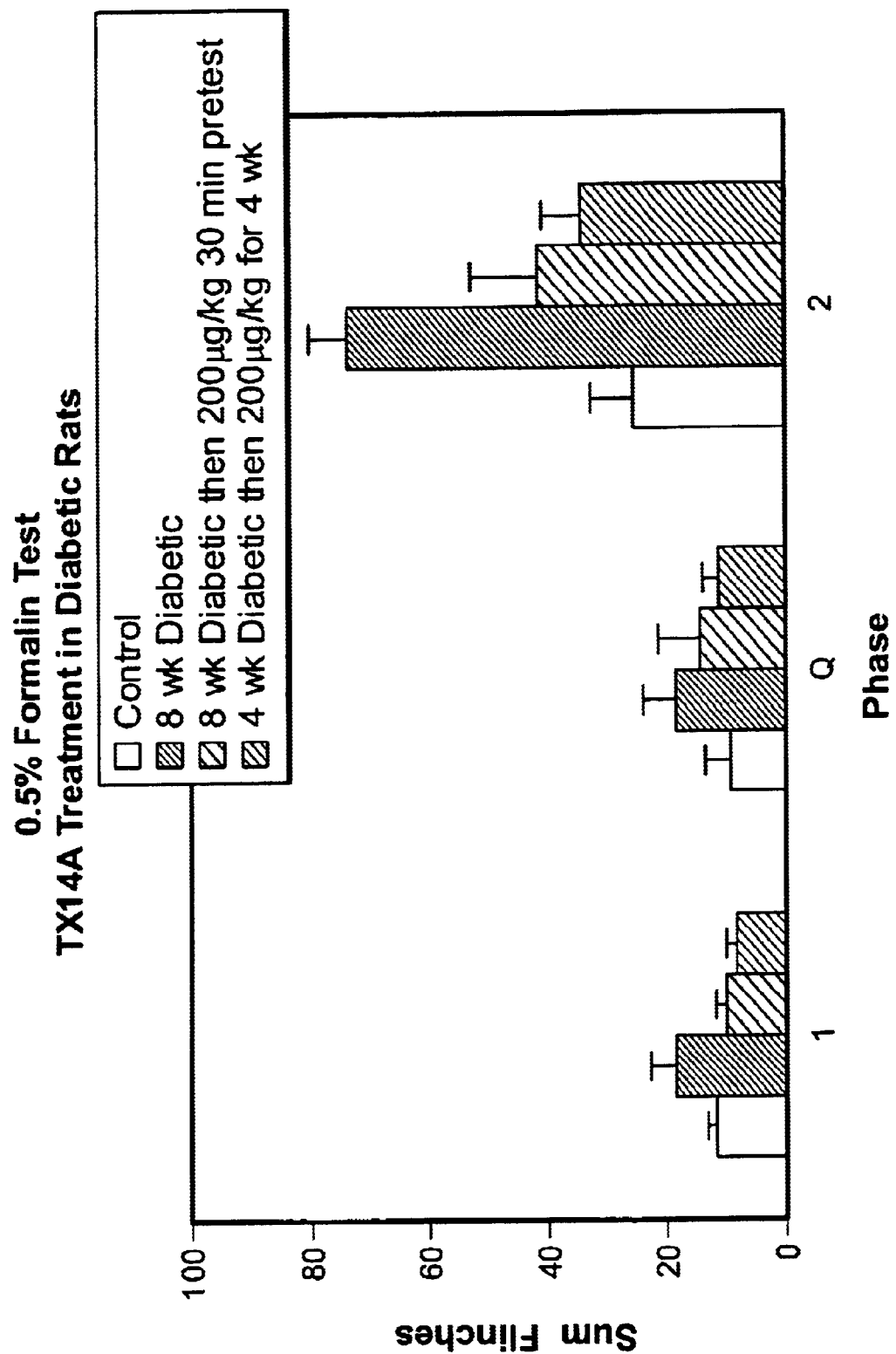
FIG. 7 shows that prosaptide TX 14(A) halts progressive slowing of sensory conduction and reverses hyperalgesia in diabetic rats. Prosaptide TX 14(A), given parenterally, reverses hyperalgesia in the diabetic rat. The anti-hyperalgesic properties of prosaptide are specific to diabetes rats rather than being a general effect on the fomalin test per se.

Prosaptide Halts Progressive Slowing of Sensory Conduction and Reverses Hyperalgesia in Diabetic Rats The results of this EXAMPLE demonstrate that the prevention of formalin-induced pain (allodynia) in diabetic rats treated with prosaptide at 200 mg/kg. The formalin testing was done after 4 weeks, of three time weekly injections, and testing was done after the last dose (last bar, FIG. 7). In a second study after 8 weeks of diabetes, prosaptide TX 14(A) (SEQ ID NO:2) was administered 30 min before testing (200 mg/kg i.p.) and reversed the hyperalgesia to a significant (p>0.05) extent (third bar, FIG. 7). These results demonstrated that prosaptide TX 14(A), given parenterally, reverses hyperalgesia in the diabetic rat, when given as a single dose after 2 months of neuropathy and latter animal testing was performed 24–48 hours after the last dose, and reversal was again highly significant (p>0.05).

In detail, the results of this EXAMPLE show that prosaptide (SEQ ID NO:2), a 14 amino acid neuroactive peptide fragment of saposin C, attenuates the decline in nerve conduction velocities (NCV) of diabetic rats in a dose-dependent manner when given from the onset of diabetes. This EXAMPLE was designed to determine whether prosaptide could also reverse conduction deficits and hyperalgesia in the formalin test pain model once these disorders are established in diabetic rats. SNCV was measured before onset of diabetes and 4–8 weeks later in groups of control, untreated diabetic and prosaptide-treated (200 $\mu$g/kg i.p. thrice weekly for the last 4 weeks) diabetic rats. Flinch responses to injection of formalin (50 $\mu$l or 0.5% or 5.0% solution) were followed for 60 min in control, 8 week untreated diabetic, 8 week diabetic treated with prosaptide (200 $\mu$g/kg i.p.) 30 min pre-test and 8 week diabetic treated with prosaptide (200 $\mu$g/kg i.p.) thrice weekly for the last 4 weeks (the last treatment being 48–72 hr pre-test). Untreated diabetic rats showed a progressive decline in SNCV so that values were significantly (P>0.05 by ANOVA with Dunnett's test) lower than controls after 4 weeks and decreased further between weeks 4 and 8. Treatment with prosaptide beginning after 4 weeks of diabetes prevents any further decline in SNCV between weeks 4 and 8 of diabetes. These animals also showed a significant (P>0.05 vs. untreated diabetic rats by ANOVA) reduction in hyperalgesia during the formalin test compared to untreated diabetics. A single bolus treatment with prosaptide given 30 min before testing in otherwise untreated 8 week diabetic rats was also effective in abolishing hyperalgesia during the formalin test whereas prosaptide in single bolus doses of up to 1 mg/kg i.p. 30 min pre-test was without effect on responses to formalin in control rats.

This EXAMPLE shows that the progression of an established SNCV disorder in diabetic rats can be halted by prosaptide. The anti-hyperalgesic properties of prosaptide are specific to diabetes rats rather than being a general effect on the formalin test per se, and prosaptide is effective either as a single dose 30 min pre-test or by chronic treatment with the final dose being at least 48 hr pre-test.

Although the invention has been described with reference to the EXAMPLES above, it should be understood that various modifications can be made without departing from the spirit of the invention. Accordingly, the invention is limited only by the following claims.

I claim:

1. A composition for alleviating neuropathic pain, comprising:

a prosaposin receptor agonist consisting of the sequence shown in SEQ ID NO:2 in a neuropathic pain alleviating effective amount; and a pharmaceutically acceptable carrier, wherein the pharmaceutical composition is in a controlled release formulation.

2. A composition for alleviating neuropathic pain, comprising:

a prosaposin receptor agonist consisting of the sequence shown in SEQ ID NO:2 in a neuropathic pain alleviating effective amount; and a pharmaceutically acceptable carrier, wherein the pharmaceutical composition is in a liposomal form.

3. A composition for alleviating neuropathic pain, comprising:

a prosaposin receptor agonist consisting of the sequence shown in SEQ ID NO:2 in a neuropathic pain alleviating effective amount; and a pharmaceutically acceptable carrier, wherein the pharmaceutical composition is in a lyophilized form.

4. A composition for alleviating neuropathic pain, comprising:

a prosaposin receptor agonist consisting of the sequence shown in SEQ ID NO:2 in a neuropathic pain alleviating effective amount; and a pharmaceutically acceptable carrier, wherein the pharmaceutical composition is in a unit dosage form.

5. The composition of any of claims 1–4, wherein the neuropathic pain results from diabetes.

* * * * *

UNITED STATES PATENT AND TRADEMARK OFFICE
CERTIFICATE OF CORRECTION

PATENT NO. : 6,849,602 B1
DATED : February 1, 2005
INVENTOR(S) : John S. O'Brien It is certified that error appears in the above-identified patent and that said Letters Patent is hereby corrected as shown below:

Title page,
Immediately above "[21] Appl. No. 08/928,074", please insert the following:
-- This patent is subject to a terminal disclaimer. --

Signed and Sealed this

Seventeenth Day of May, 2005

JON W. DUDAS
*Director of the United States Patent and Trademark Office*

SEQUENCE LISTING

```
<160> NUMBER OF SEQ ID NOS: 25

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Artificial
      peptide sequence

<400> SEQUENCE: 1

Cys Glu Phe Leu Val Lys Glu Val Thr Lys Leu Ile Asp Asn Asn Lys
  1               5                  10                  15

Thr Glu Lys Glu Ile Leu
             20

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Artificial
      Peptide Sequence
<220> FEATURE:
<221> NAME/KEY: MOD_RES
<222> LOCATION: (2)
<223> OTHER INFORMATION: Ala at position 2 is a D-enantiomer

<400> SEQUENCE: 2

Thr Ala Leu Ile Asp Asn Asn Ala Thr Glu Glu Ile Leu Tyr
  1               5                  10

<210> SEQ ID NO 3
```

```
<211> LENGTH: 12
<212> TYPE: PRT
<213> ORGANISM: Artificial Sequence
<220> FEATURE:
<223> OTHER INFORMATION: Artificial Peptide Sequence (Amino acids 18-29
      of saposin C)

<400> SEQUENCE: 3

Leu Ile Asp Asn Asn Lys Thr Glu Lys Glu Ile Leu
 1               5                  10

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Artificial
      Peptide Sequence (Mouse)

<400> SEQUENCE: 4

Cys Gln Phe Val Met Asn Lys Phe Ser Glu Leu Ile Val Asn Asn Ala
 1               5                  10                  15

Thr Glu Glu Leu Leu Tyr
            20

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Artificial
      Peptide Sequence  (Rat)

<400> SEQUENCE: 5

Cys Gln Leu Val Asn Arg Lys Leu Ser Glu Leu Ile Ile Asn Asn Ala
 1               5                  10                  15

Thr Glu Glu Leu Leu
            20

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Artificial
      Peptide Sequence  (Guinea Pig)

<400> SEQUENCE: 6

Cys Glu Tyr Val Val Lys Lys Val Met Leu Leu Ile Asp Asn Asn Arg
 1               5                  10                  15

Thr Glu Glu Lys Ile Ile
            20

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: Artificial
      Peptide Sequence (Bovine)

<400> SEQUENCE: 7

Cys Glu Phe Val Val Lys Glu Val Ala Lys Leu Ile Asp Asn Asn Arg
 1               5                  10                  15

Thr Glu Glu Glu Ile Leu
            20
```

```
<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: Artificial
      Peptide Sequence

<400> SEQUENCE: 8

Cys Glu Phe Leu Val Lys Glu Val Thr Lys Leu Ile Asp Asp Asn Lys
 1               5                  10                  15

Thr Glu Lys Glu Ile Leu
            20

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Artificial
      Peptide Sequence

<400> SEQUENCE: 9

Thr Lys Leu Ile Asp Asn Asp Lys Thr Glu Lys Glu Ile Leu
 1               5                  10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Artificial
      Peptide Sequence

<400> SEQUENCE: 10

Thr Lys Ser Ile Asp Asn Asn Lys Thr Glu Lys Glu Ile Leu
 1               5                  10

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Artificial
      Peptide Sequence (hCNTF)

<400> SEQUENCE: 11

Tyr Val Lys His Gln Gly Leu Asn Lys Asn Ile Asn Leu Asp Ser Val
 1               5                  10                  15

Asp Gly Val Pro
            20

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Artificial
      Peptide Sequence (hIL-6)

<400> SEQUENCE: 12

Glu Ala Leu Ala Glu Asn Asn Leu Asn Leu Pro Lys Met Ala Gly
 1               5                  10                  15

<210> SEQ ID NO 13
```

-continued

```
<211> LENGTH: 17
<212> TYPE: PRT
<213> ORGANISM: Artificial Sequence
<220> FEATURE:
<223> OTHER INFORMATION: Description of Artificial Sequence: Artificial
      Peptide Sequence (hIL-2)

<400> SEQUENCE: 13

Leu Gln Met Ile Leu Asn Gly Ile Asn Asn Tyr Lys Asn Pro Lys Leu
 1               5                  10                  15

Thr

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Artificial
      Peptide Sequence (hIL-3)

<400> SEQUENCE: 14

Ile Leu Met Glu Asn Asn Leu Arg Arg Pro Asn Leu
 1               5                  10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Artificial
      Peptide Sequence (hIL1-gamma)

<400> SEQUENCE: 15

Phe Tyr Leu Arg Asn Asn Gln Leu Val Ala Gly Thr Leu
 1               5                  10

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Artificial
      Peptide Sequence (hEPO)

<400> SEQUENCE: 16

Ala Glu His Cys Ser Leu Asn Glu Asn Ile Thr Val Pro Asp Thr Lys
 1               5                  10                  15

Val

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Artificial
      Peptide Sequence

<400> SEQUENCE: 17

Tyr Thr Ala Gln Gly Glu Pro Phe Pro Asn Asn Val Glu Lys Leu Cys
 1               5                  10                  15

Ala Pro

<210> SEQ ID NO 18
<211> LENGTH: 15
<212> TYPE: PRT
<213> ORGANISM: Artificial Sequence
```

-continued

```
<220> FEATURE:
<223> OTHER INFORMATION: Description of Artificial Sequence: Artificial
      Peptide Sequence (hIL-1beta)

<400> SEQUENCE: 18

Phe Asn Lys Ile Glu Ile Asn Asn Lys Leu Glu Phe Glu Ser Ala
 1               5                  10                  15

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Artificial
      Peptide Sequence (hONC-M)

<400> SEQUENCE: 19

Arg Pro Asn Ile Gly Leu Arg Asn Asn Ile Tyr Cys Met Ala Gln Leu
 1               5                  10                  15

Leu

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Artificial
      Peptide Sequence

<400> SEQUENCE: 20

Tyr Lys Glu Val Thr Lys Leu Ile Asp Asn Asn Lys Thr Glu Lys Glu
 1               5                  10                  15

Ile Leu

<210> SEQ ID NO 21
<211> LENGTH: 66
<212> TYPE: DNA
<213> ORGANISM: Artificial Sequence
<220> FEATURE:
<223> OTHER INFORMATION: Description of Artificial Sequence: Artificial
      Nucleic Acid Sequence
<220> FEATURE:
<221> NAME/KEY: CDS
<222> LOCATION: (1)..(66)

<400> SEQUENCE: 21 tgt gaa ttc ctg gtg aag gag gtg acc aag ctg att gac aac aac aag      48
Cys Glu Phe Leu Val Lys Glu Val Thr Lys Leu Ile Asp Asn Asn Lys
 1               5                  10                  15 act gag aaa gaa ata ctc                                              66
Thr Glu Lys Glu Ile Leu
            20

<210> SEQ ID NO 22
<211> LENGTH: 2749
<212> TYPE: DNA
<213> ORGANISM: Homo sapiens
<220> FEATURE:
<221> NAME/KEY: CDS
<222> LOCATION: (1)..(1572)

<400> SEQUENCE: 22 atg tac gcc ctc ttc ctc ctg gcc agc ctc ctg ggc gcg gct cta gcc      48
Met Tyr Ala Leu Phe Leu Leu Ala Ser Leu Leu Gly Ala Ala Leu Ala
 1               5                  10                  15 ggc ccg gtc ctt gga ctg aaa gaa tgc acc agg ggc tcg gca gtg tgg      96
```

```
Gly Pro Val Leu Gly Leu Lys Glu Cys Thr Arg Gly Ser Ala Val Trp
            20                  25                  30 tgc cag aat gtg aag acg gcg tcc gac tgc ggg gca gtg aag cac tgc      144
Cys Gln Asn Val Lys Thr Ala Ser Asp Cys Gly Ala Val Lys His Cys
        35                  40                  45 ctg cag acc gtt tgg aac aag cca aca gtg aaa tcc ctt ccc tgc gac      192
Leu Gln Thr Val Trp Asn Lys Pro Thr Val Lys Ser Leu Pro Cys Asp
    50                  55                  60 ata tgc aaa gac gtt gtc acc gca gct ggt gat atg ctg aag gac aat      240
Ile Cys Lys Asp Val Val Thr Ala Ala Gly Asp Met Leu Lys Asp Asn
65                  70                  75                  80 gcc act gag gag gag atc ctt gtt tac ttg gag aag acc tgt gac tgg      288
Ala Thr Glu Glu Glu Ile Leu Val Tyr Leu Glu Lys Thr Cys Asp Trp
                85                  90                  95 ctt ccg aaa ccg aac atg tct gct tca tgc aag gag ata gtg gac tcc      336
Leu Pro Lys Pro Asn Met Ser Ala Ser Cys Lys Glu Ile Val Asp Ser
            100                 105                 110 tac ctc cct gtc atc ctg gac atc att aaa gga gaa atg agc cgt cct      384
Tyr Leu Pro Val Ile Leu Asp Ile Ile Lys Gly Glu Met Ser Arg Pro
        115                 120                 125 ggg gag gtg tgc tct gct ctc aac ctc tgc gag tct ctc cag aag cac      432
Gly Glu Val Cys Ser Ala Leu Asn Leu Cys Glu Ser Leu Gln Lys His
130                 135                 140 cta gca gag ctg aat cac cag aag cag ctg gag tcc aat aag atc cca      480
Leu Ala Glu Leu Asn His Gln Lys Gln Leu Glu Ser Asn Lys Ile Pro
145                 150                 155                 160 gag ctg gac atg act gag gtg gtg gcc ccc ttc atg gcc aac atc cct      528
Glu Leu Asp Met Thr Glu Val Val Ala Pro Phe Met Ala Asn Ile Pro
                165                 170                 175 ctc ctc ctc tac cct cag gac ggc ccc cgc agc aag ccc cag cca aag      576
Leu Leu Leu Tyr Pro Gln Asp Gly Pro Arg Ser Lys Pro Gln Pro Lys
            180                 185                 190 gat aat ggg gac gtt tgc cag gac tgc att cag atg gtg act gac atc      624
Asp Asn Gly Asp Val Cys Gln Asp Cys Ile Gln Met Val Thr Asp Ile
        195                 200                 205 cag act gct gta cgg acc aac tcc acc ttt gtc cag gcc ttg gtg gaa      672
Gln Thr Ala Val Arg Thr Asn Ser Thr Phe Val Gln Ala Leu Val Glu
    210                 215                 220 cat gtc aag gag gag tgt gac cgc ctg ggc cct ggc atg gcc gac ata      720
His Val Lys Glu Glu Cys Asp Arg Leu Gly Pro Gly Met Ala Asp Ile
225                 230                 235                 240 tgc aag aac tat atc agc cag tat tct gaa att gct atc cag atg atg      768
Cys Lys Asn Tyr Ile Ser Gln Tyr Ser Glu Ile Ala Ile Gln Met Met
                245                 250                 255 atg cac atg caa ccc aag gag atc tgt gcg ctg gtt ggg ttc tgt gat      816
Met His Met Gln Pro Lys Glu Ile Cys Ala Leu Val Gly Phe Cys Asp
            260                 265                 270 gag gtg aaa gag atg ccc atg cag act ctg gtc ccc gcc aaa gtg gcc      864
Glu Val Lys Glu Met Pro Met Gln Thr Leu Val Pro Ala Lys Val Ala
        275                 280                 285 tcc aag aat gtc atc cct gcc ctg gaa ctg gtg gag ccc att aag aag      912
Ser Lys Asn Val Ile Pro Ala Leu Glu Leu Val Glu Pro Ile Lys Lys
    290                 295                 300 cac gag gtc cca gca aag tct gat gtt tac tgt gag gtg tgt gaa ttc      960
His Glu Val Pro Ala Lys Ser Asp Val Tyr Cys Glu Val Cys Glu Phe
305                 310                 315                 320 ctg gtg aag gag gtg acc aag ctg att gac aac aac aag act gag aaa     1008
Leu Val Lys Glu Val Thr Lys Leu Ile Asp Asn Asn Lys Thr Glu Lys
                325                 330                 335
```

-continued

| | |
|---|---|
| gaa ata ctc gac gct ttt gac aaa atg tgc tcg aag ctg ccg aag tcc<br>Glu Ile Leu Asp Ala Phe Asp Lys Met Cys Ser Lys Leu Pro Lys Ser<br>              340                        345                        350 | 1056 |
| ctg tcg gaa gag tgc cag gag gtg gtg gac acg tac ggc agc tcc atc<br>Leu Ser Glu Glu Cys Gln Glu Val Val Asp Thr Tyr Gly Ser Ser Ile<br>        355                        360                        365 | 1104 |
| ctg tcc atc ctg ctg gag gag gtc agc cct gag ctg gtg tgc agc atg<br>Leu Ser Ile Leu Leu Glu Glu Val Ser Pro Glu Leu Val Cys Ser Met<br>370                        375                        380 | 1152 |
| ctg cac ctc tgc tct ggc acg cgg ctg cct gca ctg acc gtt cac gtg<br>Leu His Leu Cys Ser Gly Thr Arg Leu Pro Ala Leu Thr Val His Val<br>385                        390                        395                        400 | 1200 |
| act cag cca aag gac ggt ggc ttc tgc gaa gtg tgc aag aag ctg gtg<br>Thr Gln Pro Lys Asp Gly Gly Phe Cys Glu Val Cys Lys Lys Leu Val<br>                        405                        410                        415 | 1248 |
| ggt tat ttg gat cgc aac ctg gag aaa aac agc acc aag cag gag atc<br>Gly Tyr Leu Asp Arg Asn Leu Glu Lys Asn Ser Thr Lys Gln Glu Ile<br>                    420                        425                        430 | 1296 |
| ctg gct gct ctt gag aaa ggc tgc agc ttc ctg cca gac cct tac cag<br>Leu Ala Ala Leu Glu Lys Gly Cys Ser Phe Leu Pro Asp Pro Tyr Gln<br>              435                        440                        445 | 1344 |
| aag cag tgt gat cag ttt gtg gca gag tac gag ccc gtg ctg atc gag<br>Lys Gln Cys Asp Gln Phe Val Ala Glu Tyr Glu Pro Val Leu Ile Glu<br>        450                        455                        460 | 1392 |
| atc ctg gtg gag gtg atg gat cct tcc ttc gtg tgc ttg aaa att gga<br>Ile Leu Val Glu Val Met Asp Pro Ser Phe Val Cys Leu Lys Ile Gly<br>465                        470                        475                        480 | 1440 |
| gcc tgc ccc tcg gcc cat aag ccc ttg ttg gga act gag aag tgt ata<br>Ala Cys Pro Ser Ala His Lys Pro Leu Leu Gly Thr Glu Lys Cys Ile<br>                        485                        490                        495 | 1488 |
| tgg ggc cca agc tac tgg tgc cag aac aca gag aca gca gcc cag tgc<br>Trp Gly Pro Ser Tyr Trp Cys Gln Asn Thr Glu Thr Ala Ala Gln Cys<br>                    500                        505                        510 | 1536 |
| aat gct gtc gag cat tgc aaa cgc cat gtg tgg aac taggaggagg<br>Asn Ala Val Glu His Cys Lys Arg His Val Trp Asn<br>              515                        520 | 1582 |
| aatattccat cttggcagaa accacagcat tggttttttt ctacttgtgt gtctggggga | 1642 |
| atgaacgcac agatctgttt gactttgtta taaaaatagg gctcccccac ctcccccatt | 1702 |
| tctgtgtcct ttattgtagc attgctgtct gcaagggagc ccctagcccc tggcagacat | 1762 |
| agctgcttca gtgcccctt tctctctgct agatggatgt tgatgcactg gaggtctttt | 1822 |
| agcctgccct tgcatggcgc ctgctggagg aggagagagc tctgctggca tgagccacag | 1882 |
| tttcttgact ggaggccatc aaccctcttg gttgaggcct tgttctggcc ctgacatgtg | 1942 |
| cttgggcact ggtgggcctg gcttctgag gtggcctcct gccctgatca gggaccctcc | 2002 |
| ccgctttcct gggcctctca gttgaacaaa gcagcaaaac aaaggcagtt ttatatgaaa | 2062 |
| gattagaagc ctggaataat caggcttttt aaatgatgta attcccactg taatagcata | 2122 |
| gggattttgg aagcagctgc tggtggcttg gacatcagt ggggccaagg gttctctgtc | 2182 |
| cctggttcaa ctgtgatttg gctttcccgt gtctttcctg gtgatgcctt gtttggggtt | 2242 |
| ctgtgggttt gggtgggaag agggcaatct gcctgaatgt aacctgctag ctctccgaag | 2302 |
| gccctgcggg cctggcttgt gtgagcgtgt ggacagtggg ggccgcgctg tgcctgctcg | 2362 |
| tgttgcctac atgtccctgg ctgttgaggc gctgcttcag cctgcacccc tcccttgtct | 2422 |
| catagatgct ccttttgacc ttttcaaata aatatggatg gcgagctcct aggcctctgg | 2482 |
| cttcctggta gagggcggca tgccgaaggg tctgctcggt gtggattgga tgctgggggtg | 2542 |

```
tgggggttgg aagctgtctg tggcccactt gggcacactt gggcacccac gcttctgtcc    2602
acttctggtt gccaggagac agcaagcaaa gccagcagga catgaagttg ctattaaatg    2662
gacttcgtga ttttgtttt gcactaaagt ttctgtgatt taacaataaa attctgttag    2722
ccagaaaaaa aaaaaaaaaa aaaaaaa                                         2749
```

<210> SEQ ID NO 23
<211> LENGTH: 524
<212> TYPE: PRT
<213> ORGANISM: Homo sapiens

<400> SEQUENCE: 23

```
Met Tyr Ala Leu Phe Leu Leu Ala Ser Leu Leu Gly Ala Ala Leu Ala
  1               5                  10                  15

Gly Pro Val Leu Gly Leu Lys Glu Cys Thr Arg Gly Ser Ala Val Trp
                 20                  25                  30

Cys Gln Asn Val Lys Thr Ala Ser Asp Cys Gly Ala Val Lys His Cys
             35                  40                  45

Leu Gln Thr Val Trp Asn Lys Pro Thr Val Lys Ser Leu Pro Cys Asp
         50                  55                  60

Ile Cys Lys Asp Val Val Thr Ala Ala Gly Asp Met Leu Lys Asp Asn
 65                  70                  75                  80

Ala Thr Glu Glu Glu Ile Leu Val Tyr Leu Glu Lys Thr Cys Asp Trp
                 85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
        275                 280                 285

Ser Lys Asn Val Ile Pro Ala Leu Glu Leu Val Glu Pro Ile Lys Lys
    290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335
```

```
Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
        355                 360                 365

Leu Ser Ile Leu Leu Glu Val Ser Pro Glu Leu Val Cys Ser Met
        370                 375                 380

Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
                405                 410                 415

Gly Tyr Leu Asp Arg Asn Leu Glu Lys Asn Ser Thr Lys Gln Glu Ile
                420                 425                 430

Leu Ala Ala Leu Glu Lys Gly Cys Ser Phe Leu Pro Asp Pro Tyr Gln
                435                 440                 445

Lys Gln Cys Asp Gln Phe Val Ala Glu Tyr Glu Pro Val Leu Ile Glu
        450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
                485                 490                 495

Trp Gly Pro Ser Tyr Trp Cys Gln Asn Thr Glu Thr Ala Ala Gln Cys
                500                 505                 510

Asn Ala Val Glu His Cys Lys Arg His Val Trp Asn
                515                 520

<210> SEQ ID NO 24
<211> LENGTH: 80
<212> TYPE: PRT
<213> ORGANISM: Artificial Sequence
<220> FEATURE:
<223> OTHER INFORMATION: Description of Artificial Sequence: Artificial
      Peptide Sequence

<400> SEQUENCE: 24

Ser Asp Val Tyr Cys Glu Val Cys Glu Phe Leu Val Lys Glu Val Thr
1               5                   10                  15

Lys Leu Ile Asp Asn Asn Lys Thr Glu Lys Glu Ile Leu Asp Ala Phe
            20                  25                  30

Asp Lys Met Cys Ser Lys Leu Pro Lys Ser Leu Ser Glu Glu Cys Gln
        35                  40                  45

Glu Val Val Asp Thr Tyr Gly Ser Ser Ile Leu Ser Ile Leu Leu Glu
    50                  55                  60

Glu Val Ser Pro Glu Leu Val Cys Ser Met Leu His Leu Cys Ser Gly
65                  70                  75                  80

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence:  Artificial
      Peptide Sequence
<220> FEATURE:
<221> NAME/KEY: PEPTIDE
<222> LOCATION: (1)..(12)
<223> OTHER INFORMATION: X at position 3, 11 and 12 is any amino acid; X
      at position 6 is any amino acid, but not L or R; X at
      position 8 and 10 is a charged amino acid; and X
      at position 9, when present is a charged residue
```

```
-continued

<400> SEQUENCE: 25

Leu Ile Xaa Asn Asn Xaa Thr Xaa Xaa Xaa Xaa Xaa
 1               5                  10
```